US012019081B2

(12) United States Patent
Wang et al.

(10) Patent No.: US 12,019,081 B2
(45) Date of Patent: Jun. 25, 2024

(54) METHOD FOR DETECTION AND QUANTIFICATION OF CLN3 PROTEIN

(71) Applicants: University of Kentucky Research Foundation, Lexington, KY (US); New York University, New York, NY (US)

(72) Inventors: Qingjun Wang, Lexington, KY (US); Beatrix M. Ueberheide, New York, NY (US)

(73) Assignees: University of Kentucky Research Foundation, Lexington, KY (US); New York University, New York, NY (US)

( * ) Notice: Subject to any disclaimer, the term of this patent is extended or adjusted under 35 U.S.C. 154(b) by 401 days.

(21) Appl. No.: 17/521,788

(22) Filed: Nov. 8, 2021

(65) Prior Publication Data

US 2022/0146532 A1     May 12, 2022

Related U.S. Application Data

(60) Provisional application No. 63/110,747, filed on Nov. 6, 2020.

(51) Int. Cl.
    *G01N 33/68*        (2006.01)
    *C07K 7/06*         (2006.01)
    (Continued)

(52) U.S. Cl.
    CPC ........... *G01N 33/6893* (2013.01); *C07K 7/06* (2013.01); *C07K 7/08* (2013.01); *G01N 33/58* (2013.01);
    (Continued)

(58) Field of Classification Search
    CPC ............... G01N 33/6893; G01N 33/58; G01N 30/7233; G01N 2458/15; G01N 2496/00; C07K 7/06; C07K 7/08; C07B 2200/05
    See application file for complete search history.

(56) References Cited

U.S. PATENT DOCUMENTS

| 5,869,640 A | 2/1999 | Beach |
| 2005/0164324 A1 | 7/2005 | Gygi |

(Continued)

FOREIGN PATENT DOCUMENTS

| JP | 2004/222728 | 8/2004 |
| WO | WO 2003/0016861 A2 | 2/2003 |

OTHER PUBLICATIONS

Ezaki, et al., Characterization of Cln3p, the gene product responsible for juvenile neuronal ceroid lipofuscinosis, as a lysosomal integral membrane glycoprotein, Journal of Neurochemistry, 2003, 87, 1296-1308.

(Continued)

*Primary Examiner* — Nicole M Ippolito
*Assistant Examiner* — Hanway Chang
(74) *Attorney, Agent, or Firm* — Stites & Harbison PLLC; Mandy Wilson Decker

(57) ABSTRACT

A compound and a method of detecting CLN3 are provided. The compound includes a heavy isotope labeled CLN3 proteotypic peptide. The method includes i) selecting a CLN3 proteotypic peptide that exhibits linear behavior in the mass spectrometer; ii) generating a stable isotope labeled standard; iii) spiking known amounts of the stable isotope labeled standard into a sample to form a spiked sample; iv) determining retention times and establishing calibration curves using the spiked sample; and v) detecting unlabeled selected CLN3 proteins in the sample.

20 Claims, 20 Drawing Sheets

Specification includes a Sequence Listing.

(51) Int. Cl.
*C07K 7/08* (2006.01)
*G01N 30/72* (2006.01)
*G01N 33/58* (2006.01)

(52) U.S. Cl.
CPC ...... *C07B 2200/05* (2013.01); *G01N 30/7233* (2013.01); *G01N 2458/15* (2013.01); *G01N 2496/00* (2013.01)

(56) References Cited

U.S. PATENT DOCUMENTS

| | | |
|---|---|---|
| 2005/0233327 A1 | 10/2005 | Welch |
| 2006/0218653 A1 | 9/2006 | Melville |
| 2012/0052504 A1 | 3/2012 | Boustany |
| 2013/0022981 A1 | 1/2013 | Lobel |
| 2013/0023488 A1 | 1/2013 | Wu |
| 2014/0012116 A1 | 5/2014 | Kielian |
| 2019/0032078 A1 | 1/2019 | Kielian |
| 2019/0321383 A1 | 10/2019 | Sardiello |

OTHER PUBLICATIONS

Thelen, SILAC-Based Comparative Proteomic Analysis of Lysosomes from Mammalian Cells Using LCMS/MS, Methods in Molecular Biology, 2017, pp. 1-18.

Schmidtke, Lysosomal proteome analysis reveals that CLN3-defective cells have multiple enzyme deficiencies associated with changes in intracellular trafficking, 2019, pp. 1-26.

Nelson, et al., Lack of specificity of antibodies raised against CLN3, the lysosomal/endosomal transmembrane protein mutated in juvenile Batten disease, Bioscience Reports (2017) 37, pp. 1-12.

| CLN3 Peptide | | Label | Signal Intensity | | | | | | |
|---|---|---|---|---|---|---|---|---|---|
| | | | RPE-1 | T47D | BT474 | PC-3 | DU 145 | ARPE-19 | hfRPE-M |
| P1 | LLAPLGLHLLPYSPR | Heavy | 1.E+09 | 1.E+09 | 1.E+09 | 1.E+09 | 1.E+09 | 1.E+09 | 1.E+09 |
| | | Endogenous | 5.E+04 | 7E+04 | 2.E+05 | 1.E+05 | 2.E+05 | Not detected | Not detected |
| P5 | FSDSEGEETVPEPR | Heavy | 6.E+08 | 6.E+08 | 6.E+08 | 6.E+08 | 6.E+08 | 6.E+08 | 6.E+08 |
| | | Endogenous | 1.E+05 | 1.E+05 | 1.E+05 | 1.E+05 | 1.E+05 | 1.E+05 | 1.E+05 |
| P6 | LPLLDHQGAHWK | Heavy | 1.E+08 | 1.E+08 | 1.E+08 | 1.E+08 | 1.E+08 | 1.E+08 | 1.E+08 |
| | | Endogenous | Not Detected | 4E+04 | 4.E+04 | 4.E+04 | 4.E+04 | 4.E+04 | Not Detected |
| P7 | TEAPESKPGSSSSLSLR | Heavy | 5.E+08 | 5.E+08 | 5.E+08 | 5.E+08 | 5.E+08 | 5.E+08 | 5.E+08 |
| | | Endogenous | 2.E+05 | 2.E+05 | 2.E+05 | 2.E+05 | 2.E+05 | 2.E+05 | 2.E+05 |

FIG. 2

| CLN3 Peptide | | Label | Signal Intensity | |
|---|---|---|---|---|
| | | | NIH 3T3 | FIP200+/+ MEF |
| P1 | LLAPLGLHLLPYSPR | Heavy | 2E8 | 3E8 |
| | | Endogenous | Not Detected | 6E4 |
| P2 | NTSLSHAQQYR | Heavy | 1E9 | 2E9 |
| | | Endogenous | 1E5 | Not Detected |
| P3 | EETDSEPQAPR | Heavy | 4E7 | 4E7 |
| | | Endogenous | Not Detected | Not Detected |
| P4 | SSLQCCR | Heavy | 4E6 | 4E6 |
| | | Endogenous | Not Detected | Not Detected |

METHOD FOR DETECTION AND QUANTIFICATION OF CLN3 PROTEIN

RELATED APPLICATIONS

This application claims the benefit of U.S. Provisional Application Ser. No. 63/110,747, filed Nov. 6, 2020, the entire disclosure of which is incorporated herein by this reference.

GOVERNMENT INTEREST

This invention was made with government support under grant numbers P20GM121327 and R03NS120081 awarded by the National Institutes of Health (NIH). The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Nov. 8, 2021, is named 13177N-2392US.txt and is 6.37 kilobytes in size.

TECHNICAL FIELD

The present disclosure is directed to compounds and methods for detecting and quantifying proteins. In particular, the disclosure is directed to compounds and methods for detecting and quantifying CLN3 proteins.

BACKGROUND

CLN3 is a gene that is mutated in Juvenile Neuronal Ceroid Lipofuscinosis (JNCL), which is also known as juvenile Batten disease or the CLN3 disease. JNCL is a lysosomal storage disease characterized by progressive blindness, seizures, sleep abnormalities, cognitive and motor failures, and premature death. Currently, there is no cure for the disease, nor is there a working method for CLN3 protein detection and quantification (antibody-based methods do not work as there is no working antibody[1] and no method was ever developed for probing mutant CLN3 proteins).

Accordingly, there remains a need for compounds and methods to detect and quantify CLN3 proteins (wild type and mutants) when investigating and treating JNCL.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a compound for detecting CLN3 in a sample, the compound including a heavy isotope labeled CLN3 proteotypic peptide. In some embodiments, the peptide is a tryptic peptide. In some embodiments, the heavy isotope is C or N. In some embodiments, the heavy isotope label is applied to at least one of the last two residues at the C-terminus of the peptide. In some embodiments, the C-terminal residue is at least one of K and R. In some embodiments, the heavy isotope labeled residue is $^{15}N_4,^{13}C_6$-R; $^{15}N_2,^{13}C_6$-K; $^{15}N,^{13}C_5$-P; $^{15}N,^{13}C_9$-Y; $^{15}N,^{13}C_6$-L; or $^{13}C_6$-R. In some embodiments, the compound is selected from the group consisting of 113 LLAPLGLHLLPYSP[$^{15}N_4,^{13}C_6$-R] 127; 113 LLAPLGLHLLPYS[$^{15}N,^{13}C_5$-P]R 127; 113 LLAPLGLHLLPYS[$^{15}N,^{13}C_5$-P][$^{15}N_4,^{13}C_6$-R] 127; 310 NTSLSHAQQY[$^{15}N_4,^{13}C_6$-R] 320; 310 NTSLSHAQQ[$^{15}N,^{13}C_9$-Y]R 320; 310 NTSLSHAQQ[$^{15}N,^{13}C_9$-Y][$^{15}N_4,^{13}C_6$-R] 320; 17 EETDSEPQAP[$^{15}N_4,^{13}C_6$-R] 27; 17 EETDSEPQA[$^{15}N,^{13}C_5$-P]R 27; 17 EETDSEPQA[$^{15}N,^{13}C_5$-P][$^{15}N_4,^{13}C_6$-R] 27; 11 FSDSEGEETVPEP[$^{15}N_4,^{13}C_6$-R] 24; 11 FSDSEGEETVPEP[13C$_6$-R] 24; 11 FSDSEGEETVPE[$^{15}N,^{13}C_5$-P]R 24; 11 FSDSEGEETVPE[$^{15}N,^{13}C_5$-P][$^{15}N_4,^{13}C_6$-R] 24; 256 TEAPESKPGSSSSLSL[$^{15}N_4,^{13}C_6$-R] 272; 256 TEAPESKPGSSSSLS[$^{15}N,^{13}C_6$-L]R 272; 256 TEAPESKPGSSSSLS[$^{15}N,^{13}C_6$-L][$^{15}N_4,^{13}C_6$-R] 272.

Also provided herein, in some embodiments, is a method for detecting CLN3, the method comprising i) selecting a CLN3 proteotypic peptide that exhibits linear behavior in the mass spectrometer; ii) generating a stable isotope labeled standard; iii) spiking known amounts of the stable isotope labeled standard into a sample to form a spiked sample; iv) determining retention times and establishing calibration curves using the spiked sample; and v) detecting unlabeled selected CLN3 proteins in the sample. In some embodiments, the CLN3 proteotypic peptide is unique in mouse, human, or other proteomes. In some embodiments, the stable isotope labeled standard corresponds to a wild-type CLN3 protein. In some embodiments, the stable isotope labeled standard corresponds to a mutant CLN3 protein. In some embodiments, the proteotypic peptide is a tryptic peptide. In some embodiments, the stable isotope labeled standard includes one or more of the compounds disclosed herein.

In some embodiments, establishing internal calibration curves includes determining at least one of a lower limit of detection, a linear detection range, and LC-MS parameters. In some embodiments, detecting the unlabeled selected CLN3 peptides in the sample includes mixing a known concentration of the isotope labeled standard into a sample; eluting the peptides from the sample; and determining whether the isotope labeled standard co-elutes with an unlabeled proteotypic peptide from the unlabeled selected CLN3 proteins. In some embodiments, the method further includes quantifying the unlabeled selected CLN3 proteins in the sample. In some embodiments, quantifying the unlabeled selected CLN3 proteins comprises calculating the amount of unlabeled proteotypic peptide based on the intensity of the corresponding isotope labeled standard of known concentration. In some embodiments, the method further includes mixing a known concentration of an additional isotope labeled standard into the sample, the additional isotope labeled standard corresponding to a protein that is present in wild-type CLN3 but not mutated CLN3; eluting the peptides from the sample; determining whether the eluted peptides include an unlabeled proteotypic peptide from the unlabeled selected CLN3 protein that co-elutes with the isotope labeled standard; and determining whether the detected peptides include mutated CLN3 protein using the additional isotope labeled standard. In some embodiments, the unlabeled selected CLN3 proteins are mutant proteins. In some embodiments, generating the stable isotope labeled standard includes generating a heavy isotope labeled mutant peptide; and detecting the unlabeled selected mutant CLN3 proteins in the sample includes mixing a known concentration of the heavy isotope labeled mutant peptide into the sample; eluting the peptides from the sample; and determining whether the heavy isotope labeled mutant peptide co-elutes with an unlabeled proteotypic peptide from the unlabeled selected mutant CLN3 proteins. In some embodiments, the method further includes determining whether a subject has a disease based upon the amount of CLN3 protein expressed or the presence of a mutated CLN3 protein.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIG. 2 shows a table illustrating a summary of human cell line results with the stable isotope labeled standards spiked in. Signals for heavy peptides represent 1 pmole. From this table, amounts of endogenous CLN3 peptides in 500 ng total protein loaded can be calculated from the signals of the known concentration of the stable isotope labeled standards. Note, P1 peptide can be used for quantifying human or mouse, wild type (WT) or 1 kb deletion mutant (1 kb) CLN3 protein; P5, P5' and P6 can be used for quantifying human WT or 1 kb deletion mutant CLN3 protein; and P7 can be used for quantifying human WT CLN3 protein.

FIG. 10 shows a table illustrating a summary of mouse cell line results with the stable isotope labeled standards spiked in.

FIG. 11 shows graphs illustrating NIH 3T3 samples (mouse embryonic fibroblast cell line; 500 ng total protein) with the stable isotope labeled standards (1 pmole for each of the 8 heavy CLN3 peptides) spiked in.

FIG. 12 shows graphs illustrating FIP200+/+MEF samples (mouse embryonic fibroblast cell line; 500 ng total protein) with the stable isotope labeled standards (1 pmole for each of the 8 heavy CLN3 peptides) spiked in.

Figure 1:
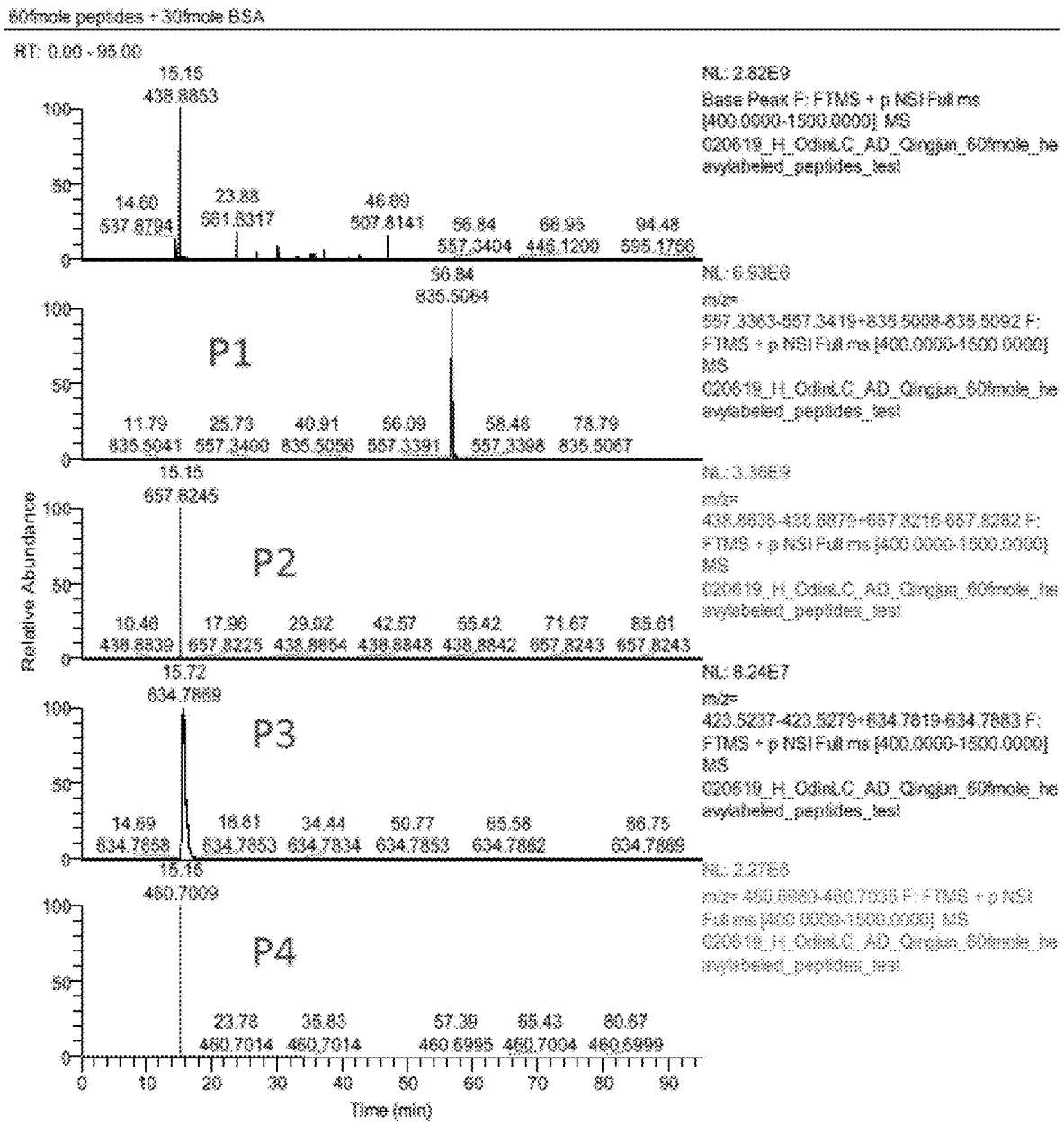
FIG. 1 shows graphs illustrating elution times and purities of 8 synthesized heavy stable isotope labeled CLN3 peptides. Each peptide was resuspended in 0.5% acetic acid and 60 fmole was injected on column (30 fmole BSA digest as carrier).
Figure 1:
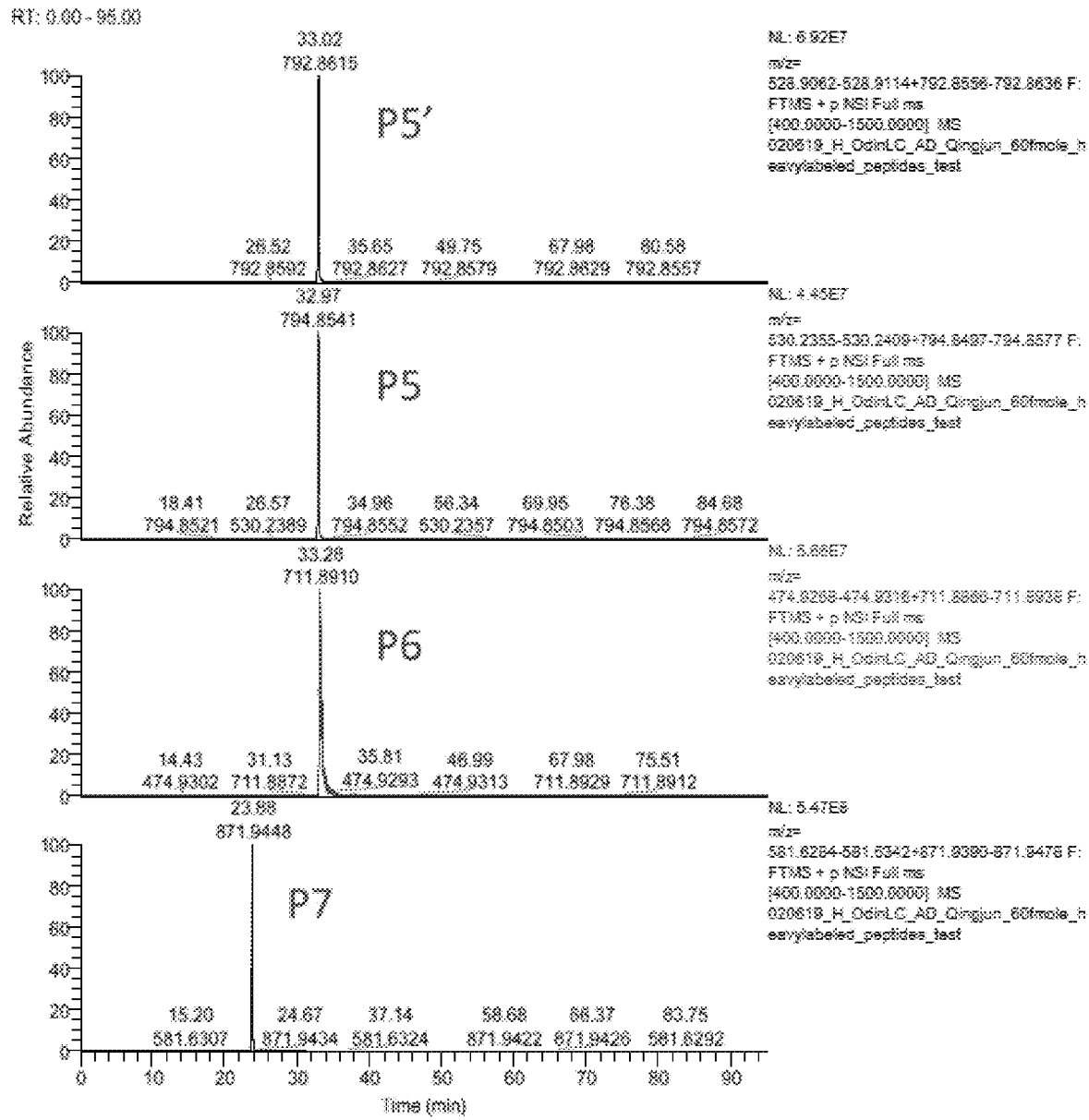
Figure 3:
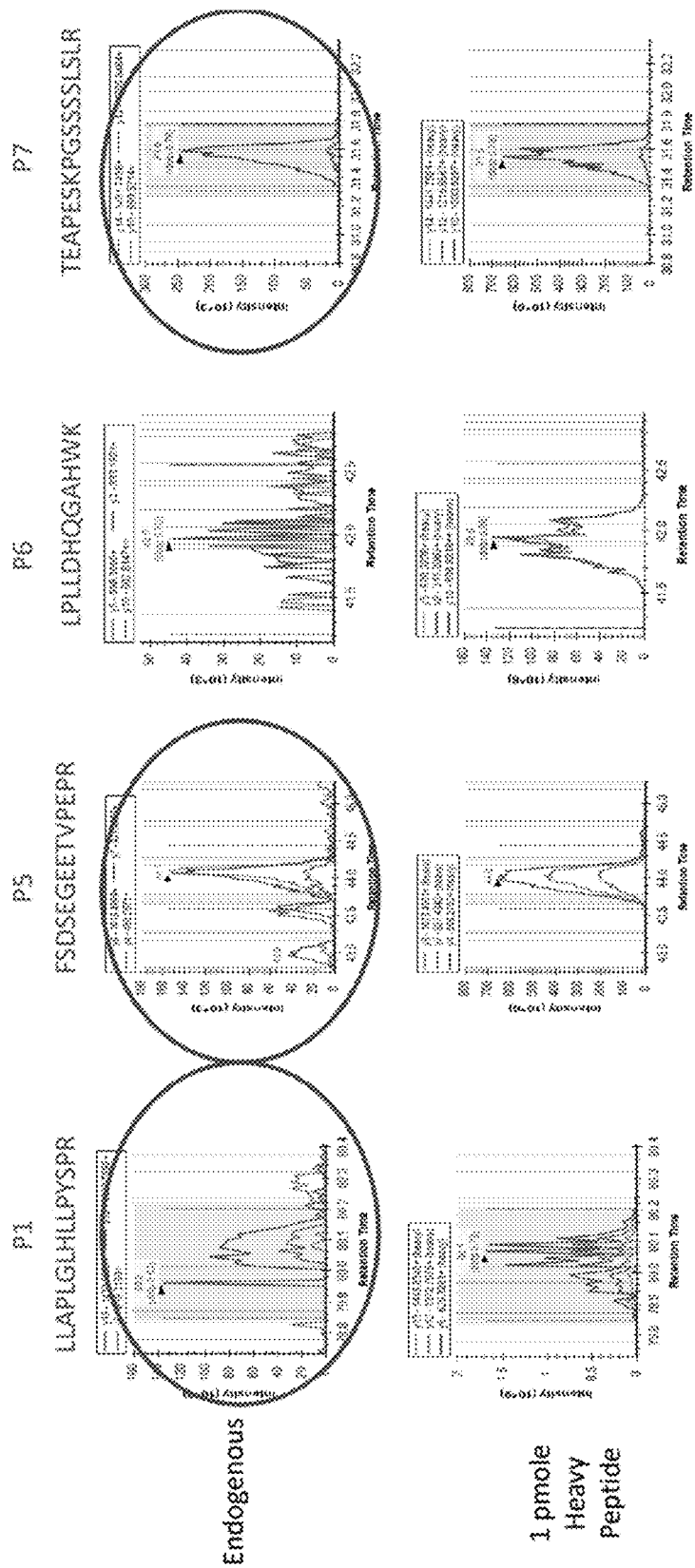
FIG. 3 shows graphs illustrating RPE-1 samples (human retinal pigment epithelial cell line; 500 ng total protein) with the stable isotope labeled standards (1 pmole for each of the 8 heavy CLN3 peptides) spiked in. Based on these results, amounts of endogenous WT CLN3 in RPE-1 cell extract (500 ng total protein) are in the sub-fmole range.
Figure 4:
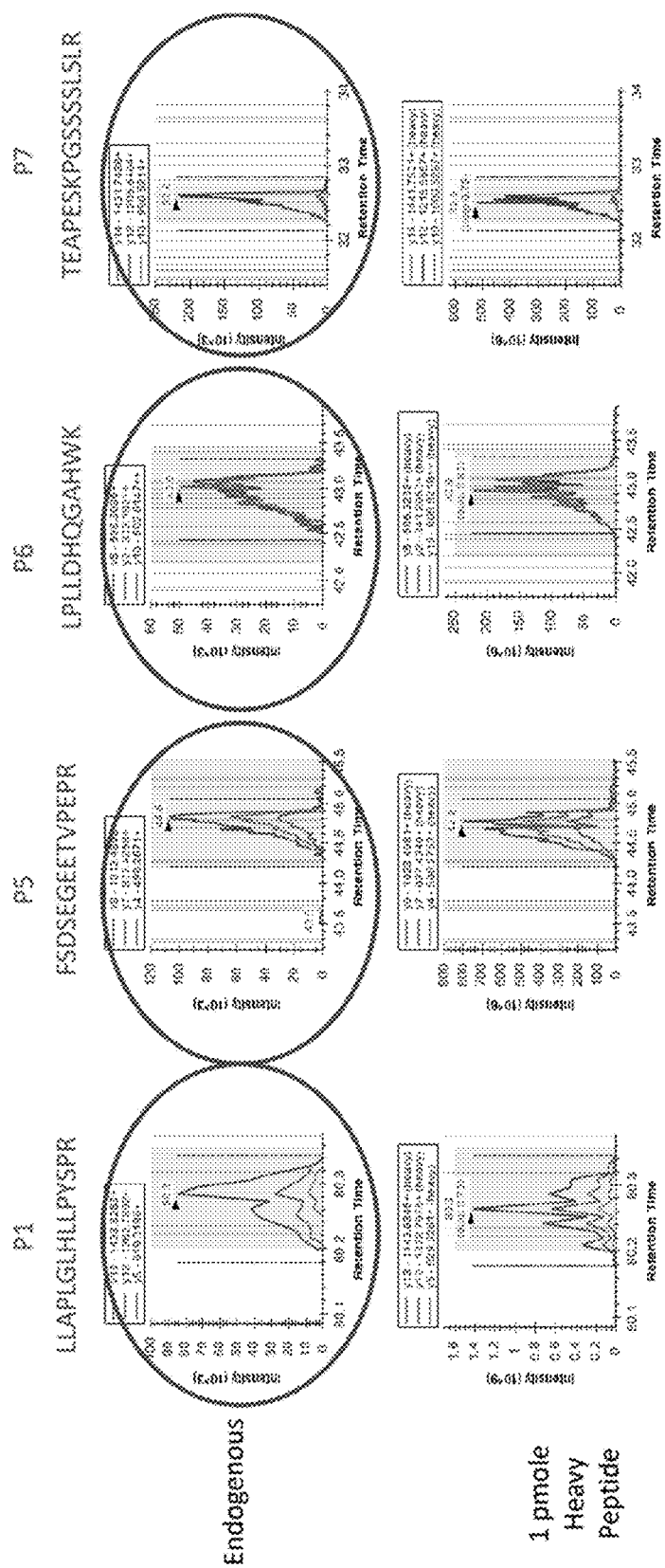
FIG. 4 shows graphs illustrating T47D samples (human breast cancer cell line; 500 ng total protein) with the stable isotope labeled standards (1 pmole for each of the 8 heavy CLN3 peptides) spiked in. Based on these results, amounts of endogenous WT CLN3 in T47D cell extract (500 ng total protein) are in the sub-fmole range.
Figure 5:
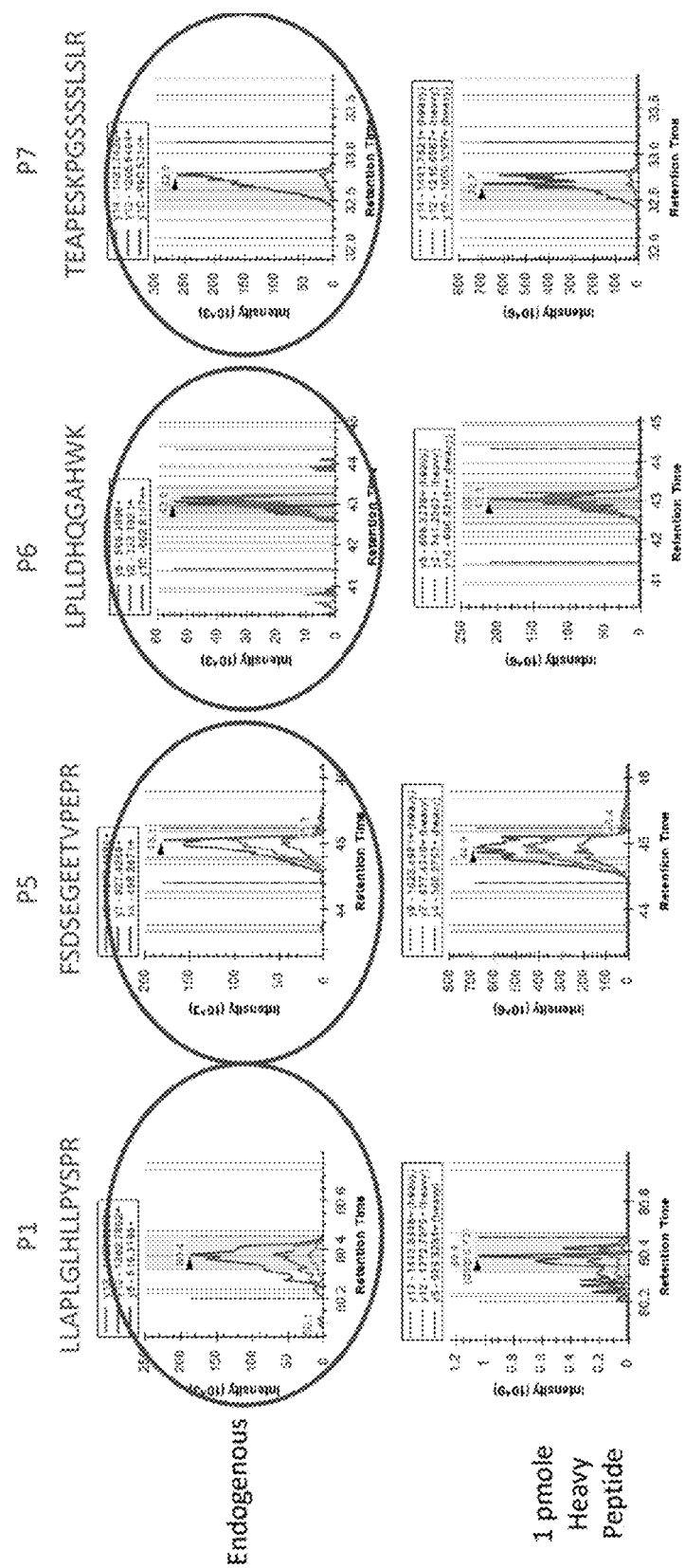
FIG. 5 shows graphs illustrating BT474 samples (human breast cancer cell line; 500 ng total protein) with the stable isotope labeled standards (1 pmole for each of the 8 heavy CLN3 peptides) spiked in. Based on these results, amounts of endogenous WT CLN3 in BT474 cell extract (500 ng total protein) are in the sub-fmole range.
Figure 6:
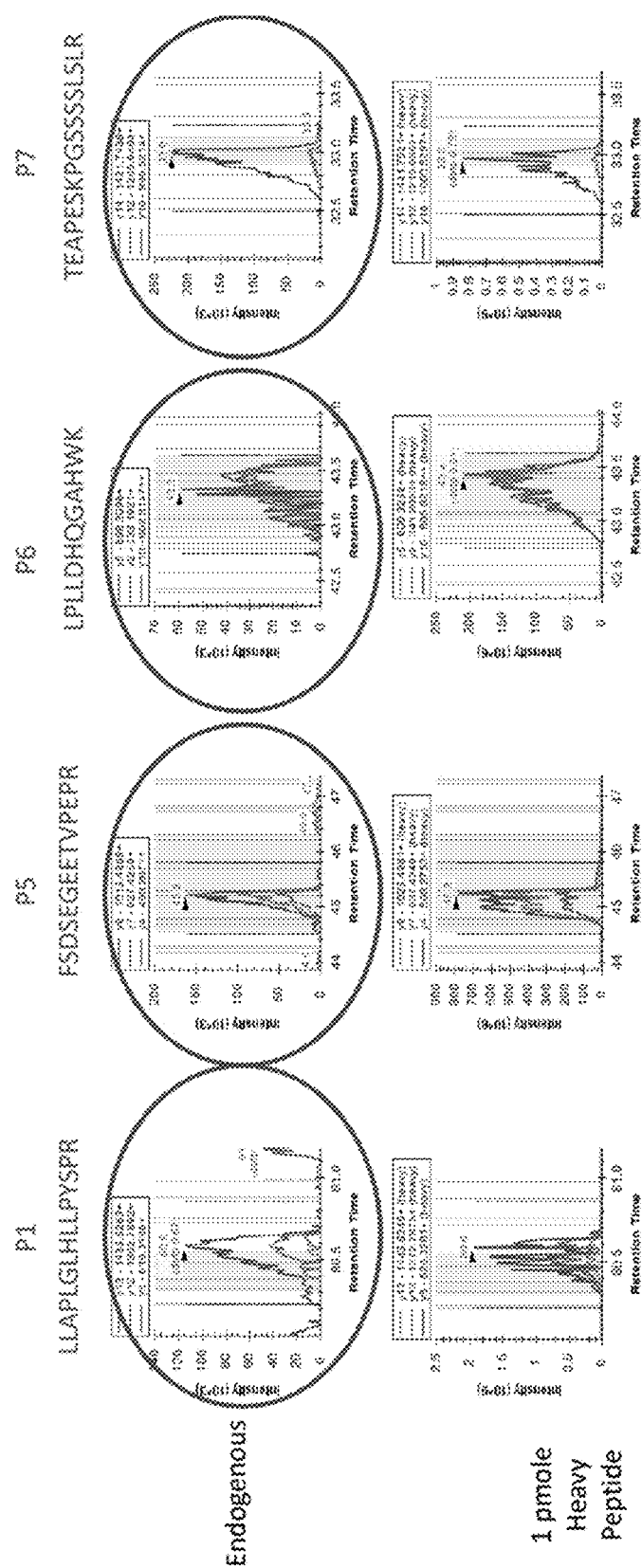
FIG. 6 shows graphs illustrating PC-3 samples (human prostate cancer cell line; 500 ng total protein) with the stable isotope labeled standards (1 pmole for each of the 8 heavy CLN3 peptides) spiked in. Based on these results, amounts of endogenous WT CLN3 in PC3 cell extract (500 ng total protein) are in the sub-fmole range.
Figure 7:
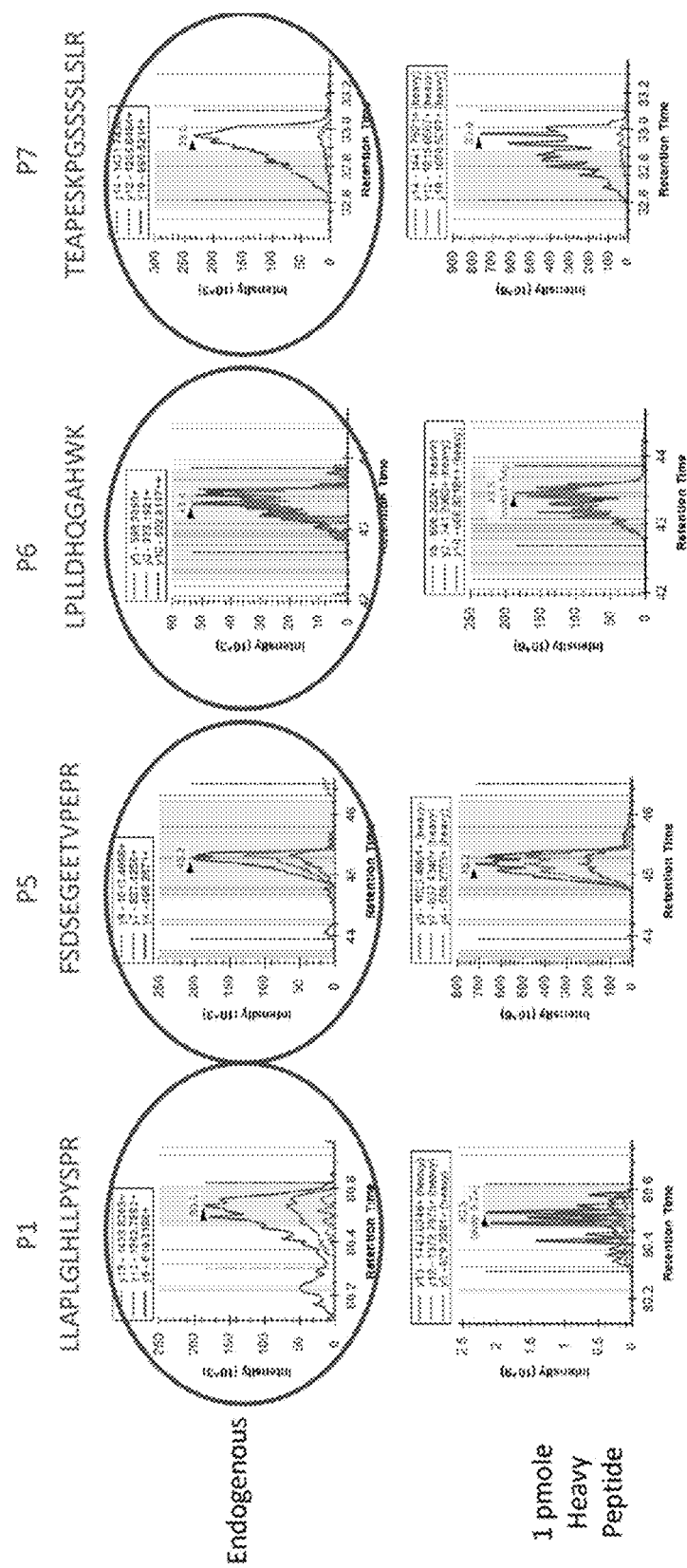
FIG. 7 shows graphs illustrating DU145 samples (human prostate cancer cell line; 500 ng total protein) with the stable isotope labeled standards (1 pmole for each of the 8 heavy CLN3 peptides) spiked in. Based on these results, amounts of endogenous WT CLN3 in DU145 cell extract (500 ng total protein) are in the sub-fmole range.
Figure 8:
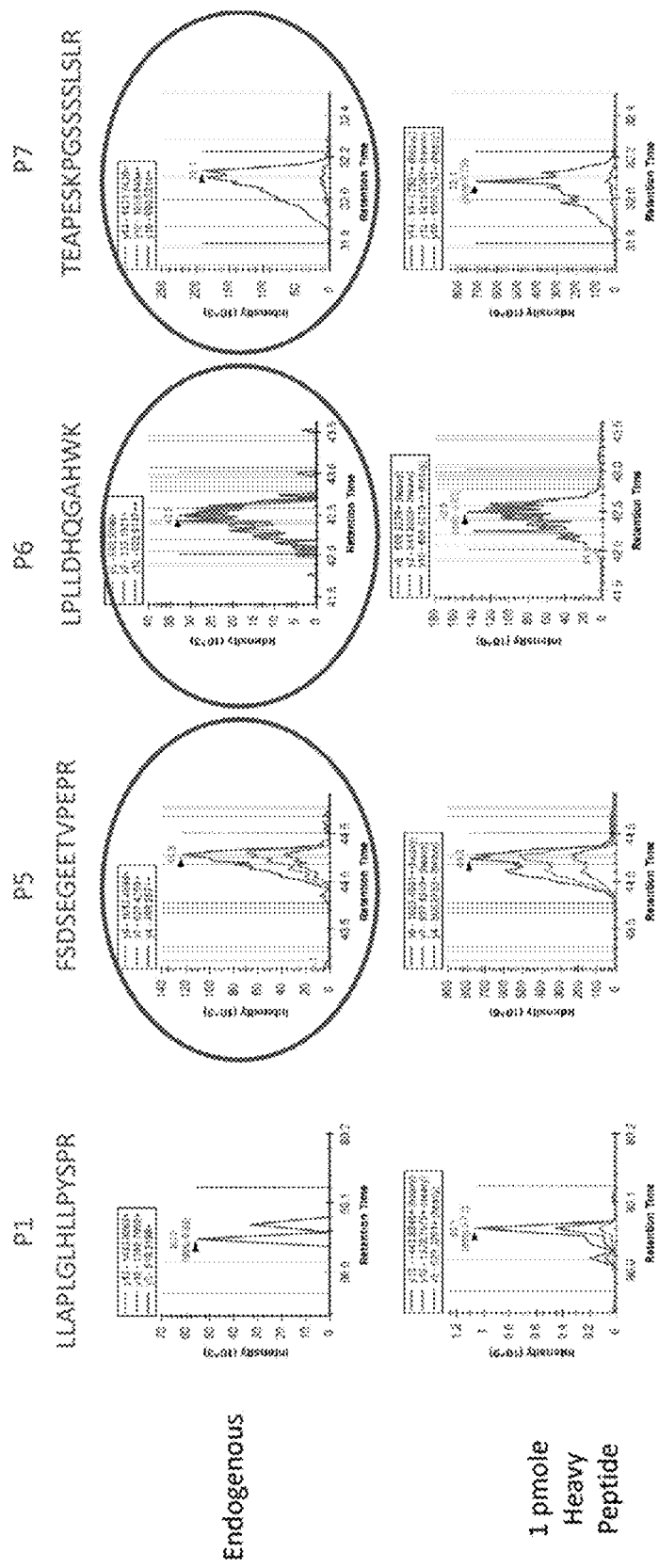
FIG. 8 shows graphs illustrating ARPE19 samples (human retinal pigment epithelial cell line; 500 ng total protein) with the stable isotope labeled standards (1 pmole for each of the 8 heavy CLN3 peptides) spiked in. Based on these results, amounts of endogenous WT CLN3 in ARPE19 cell extract (500 ng total protein) are in the sub-fmole range.
Figure 9:
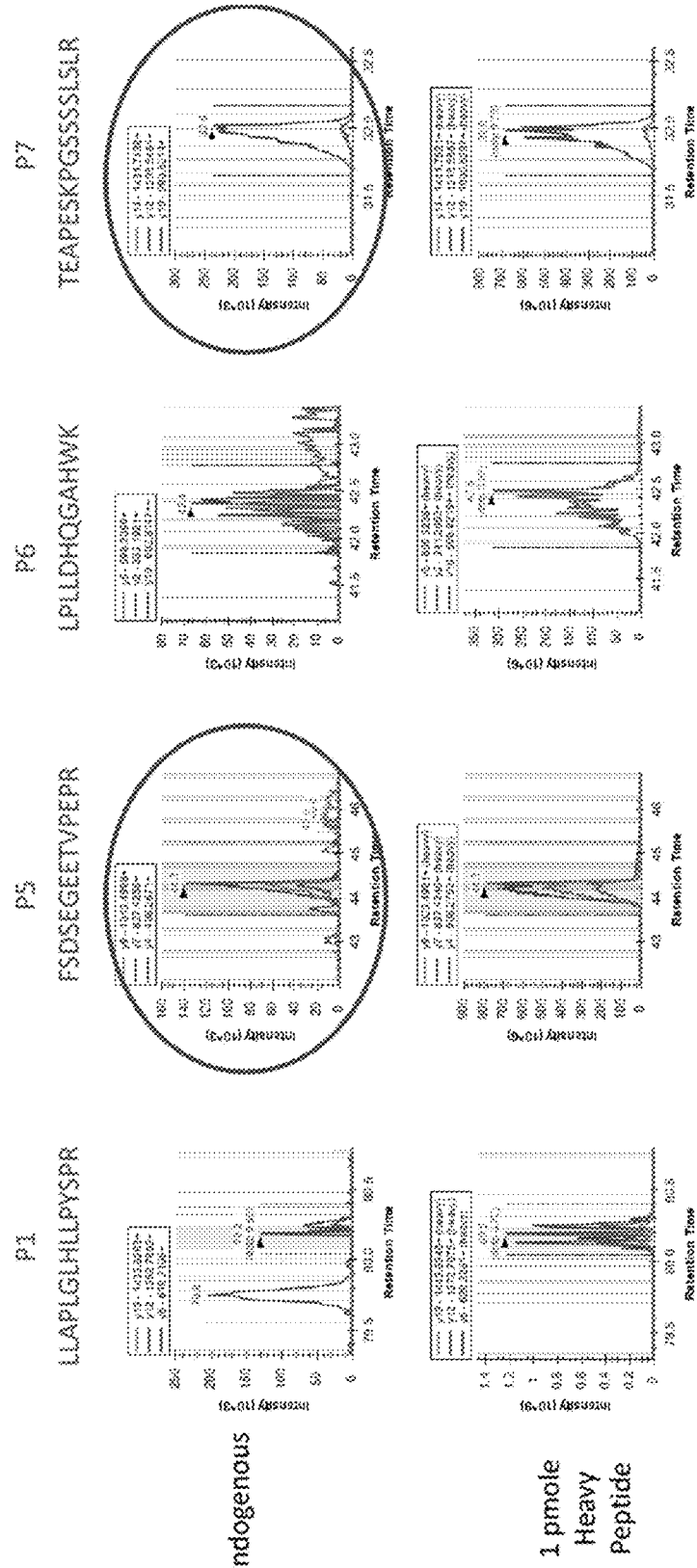
FIG. 9 shows graphs illustrating hfRPE-M samples (human fetal retinal pigment epithelial cell line; 500 ng total protein) with the stable isotope labeled standards (1 pmole for each of the 8 heavy CLN3 peptides) spiked in. Based on these results, amounts of endogenous WT CLN3 in hfRPE-M cell extract (500 ng total protein) are in the sub-fmole range.

showed linear responses. (D) Peptide 6 (P6) did not show linear responses. (E) Peptide 7 (P7) showed linear responses.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DEFINITIONS

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "optional" or "optionally" means that the subsequently described event or circumstance can or cannot occur, and that the description includes instances where said event or circumstance occurs and instances where it does not.

As used herein, the term "patient" refers to a subject afflicted with a disease or disorder. A patient includes human and veterinary subjects.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, rodent, or fish. The term does not denote a particular age or sex. Thus, adult and newborn subjects, as well as fetuses, whether male or female, are intended to be covered.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rear-

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Provided herein are compounds and methods for detecting and/or quantifying CLN3 proteins. In some embodiments, the method includes i) selecting one or more CLN3 proteotypic peptides that exhibit linear behavior in the mass spectrometer; ii) generating stable isotope labeled standards suitable for detection of the CLN3 proteins; iii) establishing a calibration curve; and iv) detecting and quantifying unlabeled CLN3 peptides. In some embodiments, the CLN3 proteins include WT and/or mutant CLN3 proteins. For example, in one embodiment, the method includes detecting and/or quantifying both WT and mutant CLN3 proteins simultaneously.

Referring to the first step, the one or more peptides include any suitable CLN3 peptide that may be generated by any specific proteolytic enzyme and/or by any chemical means of generating peptides. In some embodiments, the CLN3 proteotypic peptide(s) are unique in the mouse, human, dog, sheep, pig, bovine, zebrafish, or other proteomes. In some embodiments, the one or more CLN3 peptides include tryptic peptides. For example, in one embodiment, the one or more peptides include, but are not limited to, 113 LLAPLGLHLLPYSPR 127 (SEQ ID NO: 1; residues 113-127 in the WT full length), 310 NTSLSHAQQYR 320 (SEQ ID NO: 2; residues 310-320 in the WT full length), 17 EETDSEPQAPR 27 (SEQ ID NO: 3; residues 17-27 in the WT full length), 11 FSDSEGEETVPEPR 24 (SEQ ID NO: 4; residues 11-24 in the WT full length), 256 TEAPESKPGSSSSLSLR 272 (SEQ ID NO: 5; residues 256-272 in the WT full length), or a combination thereof. In some embodiments, the peptides are labeled with any suitable label, such as, but not limited to, a heavy stable isotope label on any one or more amino acid residues. Suitable heavy isotopes include, but are not limited to, $[^{15}N_4,^{13}C_6]$, $[^{15}N_2,^{13}C_6]$, $[^{15}N,^{13}C_5]$, $[^{15}N,^{13}C_9]$, $[^{15}N,^{13}C_6]$, $[^{13}C_6]$, any other suitable heavy isotope, or a combination thereof. Although described herein primarily with respect to tryptic peptides, as will be appreciated by those skilled in the art, the disclosure is not limited to those peptides and includes any other suitable peptide generated by other proteolytic enzymes with specific cleavage sites, such as, but not limited to, LysC, GluC, AspN, or any other suitable enzyme.

Turning to the second step, the stable isotope labeled standards include any isotope labeled standard suitable for detection of the CLN3 proteins. In some embodiments, generating the isotopic standards includes labeling a desired (e.g., dominant) fragment ion. In one embodiment, for example, generating the isotopic standards includes selecting amino acids corresponding to the desired fragment ions and applying the label (also referred to herein as a "tag") to the selected amino acids. Applying the label to amino acids corresponding to the desired fragment ensures that the desired fragment ions are the ones that carry the tag. In some embodiments, the C-terminal residues are labeled. The C-terminal residues include any one or more of the final 5 residues, the final 4 residues, the final 3 residues, and/or the final 2 residues at the C-terminal of the peptide. For example, in one embodiment, the C-terminal residues K and R of tryptic peptides are labeled. In another embodiment, the C-terminal residue labeled tryptic peptides include, but are not limited to, 113 LLAPLGLHLLPYSP[$^{15}N_4,^{13}C_6$-R] 127 (SEQ ID NO: 6), 113 LLAPLGLHLLPYS[$^{15}N,^{13}C_5$-P]R 127 (SEQ ID NO: 7), 113 LLAPLGLHLLPYS[$^{15}N,^{13}C_5$-P][$^{15}N_4,^{13}C_6$-R] 127 (SEQ ID NO: 8), 310 NTSLSHAQQY[$^{15}N_4,^{13}C_6$-R] 320 (SEQ ID NO: 9), 310 NTSLSHAQQ[$^{15}N,^{13}C_9$-Y]R 320 (SEQ ID NO: 10), 310 NTSLSHAQQ[$^{15}N,^{13}C_9$-Y][$^{15}N_4,^{13}C_6$-R] 320 (SEQ ID NO: 11), 17 EETDSEPQAP[$^{15}N_4,^{13}C_6$-R] 27 (SEQ ID NO: 12), 17 EETDSEPQA[$^{15}N,^{13}C_5$-P]R 27 (SEQ ID NO: 13), 17 EETDSEPQA[$^{15}N,^{13}C_5$-P][$^{15}N_4,^{13}C_6$-R] 27 (SEQ ID NO: 14), 11 FSDSEGEETVPEP[$^{15}N_4,^{13}C_6$-R] 24 (SEQ ID NO: 15), 11 FSDSEGEETVPEP[$^{13}C_6$-R] 24 (SEQ ID NO: 15), 11 FSDSEGEETVPE[$^{15}N,^{13}C_5$-P]R 24 (SEQ ID NO: 16), 11 FSDSEGEETVPE[$^{15}N,^{13}C_5$-P][$^{15}N_4,^{13}C_6$-R] 24 (SEQ ID NO: 17), 256 TEAPESKPGSSSSLSL[$^{15}N_4,^{13}C_6$-R] 272 (SEQ ID NO: 18), 256 TEAPESKPGSSSSLS[$^{15}N,^{13}C_6$-L]R 272 (SEQ ID NO: 19), 256 TEAPESKPGSSSSLS[$^{15}N,^{13}C_6$-L][$^{15}N_4,^{13}C_6$-R] 272 (SEQ ID NO: 20), or a combination thereof.

The labeled peptides may be synthesized using any suitable synthesis method, such as, but not limited to, solid phase peptide synthesis. For example, in some embodiments, stable isotope-labeled amino acids (e.g., [$^{15}N_4,^{13}C_6$-R], [$^{15}N_2,^{13}C_6$-K], [$^{15}N,^{13}C_5$-P], [$^{15}N,^{13}C_9$-Y], [$^{15}N,^{13}C_6$-L], and [$^{13}C_6$-R], where R is arginine, K is lysine, P is proline, Y is tyrosine, and L is leucine) are added during peptide synthesis, which results in the C-terminal amino acid residue for each peptide being labeled. Additionally or alternatively, in some embodiments, synthesizing a labeled peptide with two cysteines includes adding cysteines with carboxyamidomethylation, as the endogenous peptide is alkylated with carboxyamidomethylation during sample preparation. Although discussed herein primarily with respect to labeling with C or N, as will be appreciated by those skilled in the art, any other suitable heavy isotope may be used. Similarly, while discussed herein primarily with respect to labeling of K and R as the last C-terminal residues when using trypsin digestion, the disclosure is not so limited and may include labeling of any other C-terminal residues corresponding to other proteolytic digestion. Furthermore, while discussed herein primarily with respect to labeling of the last C-terminal residues, the disclosure is again not so limited and may include labeling of any other residue in such a way that at least some of the resulting fragment ions, namely the dominant ones, carry the isotope tag.

In the third step, establishing the calibration curve facilitates accurate and sensitive detection and quantification of CLN3 proteins. In some embodiments, establishing the calibration curve includes determining a lower limit of detection, linear detection ranges, and/or LC-MS parameters for sensitive and accurate quantification of unlabeled CLN3 proteins. In some embodiments, the calibration curve is established using a dilution series of a single labeled peptide. Alternatively, in some embodiments, the calibration curve is established using different amounts of different heavy versions of the same unlabeled peptides. A calibration curve is established for each specific CLN3 peptide (both labeled and unlabeled), and endogenous unlabeled CLN3 peptides have the same elution times as the corresponding labeled peptides. As such, the corresponding endogenous peptides can be detected using the retention time information from the labeled peptides. As will be appreciated by those skilled in the art, any suitable LC system (e.g., Easy-nLC 1200 (Thermo Scientific)) may be used for this analysis.

Once the isotope labeled standards have been generated, detecting and/or quantifying the CLN3 peptides includes first mixing a known concentration of the labeled standard into a sample including the endogenous (unlabeled) CLN3 peptides to be quantified (also referred to herein as "spiking" the sample with the labeled peptides), eluting the labeled and unlabeled peptides from the sample, and detecting and/or quantifying the eluted peptides. In some embodiments, detecting and quantifying the unlabeled CLN3 peptides includes matching the concentrations of the calibration curve to the endogenous CLN3 peptides, such that the endogenous concentrations fall within the linear range of the respective labeled peptide standards. Since the amount of labeled peptide in the sample is known, and the labeled and unlabeled peptides have the same elution times, the amounts of unlabeled peptides can be calculated from the integrated mass spectral signals (peak areas) of unlabeled and labeled peptides (see FIG. 13). In some embodiments, difference between the amount of unlabeled peptide common to wild-type and mutant CLN3 proteins and the amount of unlabeled peptide specific to wild-type CLN3 protein corresponds to the amount of unlabeled peptide specific to mutant CLN3 protein in the sample.

The labeled and unlabeled peptides are eluted using any suitable device and/or method, such as, but not limited to, through liquid chromatography (LC). Similarly, the eluted peptides are detected and/or quantified using any suitable device and/or method, such as, but not limited to, through mass spectrometry. For example, in some embodiments, the detecting and/or quantifying is done through liquid chromatography coupled to mass spectrometry or direct infusion mass spectrometry. Any high resolution mass spectrometer is suitable for this workflow, using quantitation protocols such as, but not limited to, parallel reaction monitoring (PRM) or selected reaction monitoring (SRM). In some embodiments, the PRM assay includes a hybrid quadrupole-Orbitrap (q-OT) mass spectrometer or a quadrupole time-of-flight (q-TOF) mass spectrometer. For example, in one embodiment, the method includes spiking a sample including unlabeled CLN3 peptides with a known amount of isotope-labeled tryptic peptides, eluting the spiked sample with an EASY-nLC 1200 (Thermo Scientific) LC system, and quantifying peptides in the sample with a hybrid quadrupole-Orbitrap (q-OT) mass spectrometer (or a quadrupole time-of-flight (q-TOF) mass spectrometer). Alternatively, in some embodiments, the SRM assay includes a triple-quadrupole (QQQ) or a hybrid quadrupole-linear ion trap (QTrap) mass spectrometer. For example, in one embodiment, the SRM assay is used to detect and/or quantify CLN3 proteolytic peptides digested by proeolytic enzymes other than trypsin.

Additionally or alternatively, in some embodiments, the method includes quantifying the amount of WT and mutant proteins. In some embodiments, the method includes comparing the amounts of protein detected by peptides retained in the mutant to amounts of protein detected by peptides only present in the WT. For example, juvenile Batten disease patients include a 1 kb-deletion mutation in the CLN3 gene, which leads to a shorter protein with the first 153 amino acids the same as the WT CLN3 followed by additional new C-terminal 28 amino acids. Since the N-terminal portion of the mutant includes the same sequence as the N-terminal portion of the WT, peptides in the N-terminal portion (e.g., P1, P5/P5', and P6 in human CLN3; P1 and P3 in mouse CLN3) are retained in the mutant. In contrast, since the C-terminal portion of the mutant differs from the C-terminal portion of the WT, peptides in the C-terminal portion (P7 in human CLN3; P2 and P4 in mouse CLN3) are not retained in the mutant. Therefore, the amounts of WT and mutant proteins can be quantified by comparing the amounts detected by P1, P5, P5', or P6 (i.e., both the WT and mutant) to the amounts detected by P2 or P7 (i.e., the WT only).

Although discussed primarily with respect to using WT peptides to quantify mutant CLN3 based upon the knowledge that 1 kb or other mutants have at least one of the 7 peptides missing, the disclosure is not so limited and includes any other suitable method for detecting and/or quantifying mutants. For example, in some embodiments, the method includes detecting and quantifying a mutant CLN3 protein with a point mutation within one of the 7 peptide sequences. In such embodiments, the method includes synthesizing an additional standard including a heavy isotope labeled mutant peptide, then detecting and directly quantifying the endogenous mutant peptide using the additional standard. Alternatively, in certain embodiments where a point mutation does not fall within one of the 7 peptides, other proteolytic enzymes may be used to include the point mutation in one of the CLN3 peptide unique in the proteome. In such embodiments, the additional standard including a heavy isotope labeled mutant peptide is synthesized based upon the location of the point mutation and the proteolytic enzyme used.

As discussed above, the eluted peptides detected and/or quantified according to this method include labeled WT and mutant peptides, unlabeled WT peptides that are also present in mutant proteins, unlabeled WT peptides that are not present in mutant proteins (e.g., 1 kb mutant or any other suitable mutant), and/or unlabeled mutant peptides. Additionally or alternatively, in some embodiments, the method includes simultaneously quantifying both WT and mutant CLN3 proteins. Accordingly, the methods disclosed herein provide clinical applications as a critical tool to quantify CLN3 protein levels in healthy individuals to determine gender differences, age differences, developmental alterations and tissue distributions, quantify CLN3 protein levels in subjects that may have a cancer where CLN3 protein is overexpressed, quantify WT or mutant CLN3 protein levels in subjects that may have JNCL where CLN3 protein is lost and/or mutated, and quantify CLN3 protein levels during CLN3 disease treatments (e.g., determine CLN3 protein levels in JNCL patients treated with CLN3 gene therapy, antisense oligo therapy (for in-frame splicing), small molecular therapy BBDF101 (for boosting lysosomal biogenesis), and proteostasis therapy). Additionally, the methods provide a tool for CLN3 researchers to detect and quantify CLN3 protein in cells and tissues (e.g., tissue biopsies, cell cultures) from mice, humans, and potentially other species; determine the subcellular distribution of WT and mutant CLN3 proteins when coupling these methods to subcellular fractionation; and/or determine the subcellular distribution of WT and mutant CLN3 proteins when coupling these method to imaging mass spectrometry. Furthermore, the stable isotope-labeled CLN3 peptides and other related products (e.g., QconCAT concatemer) disclosed herein have good mass spectrometric responses and can be independently used as quantification standards.

Also provided herein are methods of detecting a disease involving CLN3 in a subject. In some embodiments, the method includes obtaining a sample from the subject, selecting one or more CLN3 proteotypic peptides of interest that exhibit linear behavior in the mass spectrometer; generating stable isotope labeled standards suitable for detection of the selected CLN3 proteins; establishing a calibration curve; and detecting and/or quantifying unlabeled CLN3 peptides. In some embodiments, the selected CLN3 proteotypic peptide is a CLN3 peptide that is abnormally expressed (e.g., over or under expressed) in the disease. In such embodiments, the method includes quantifying the amount of the peptide in the sample, determining if the amount is outside a normal range, and identifying the subject as having the disease when the amount is abnormal. For example, in some embodiments, the method includes identifying a subject with a cancer involving overexpression of CLN3 when the amount of CLN3 in the sample is determined to be above a normal amount. In some embodiments, the selected CLN3 proteotypic peptide is a CLN3 peptide that is mutated in the disease. In such embodiments, the method includes detecting and/or quantifying the mutated CLN3 peptide in the sample, and identifying the subject as having the disease when the mutated CLN3 peptide is present in the sample. In some embodiments, the disease includes any disease involving mutated CLN3, such as, but not limited to, a lysosomal disease involving mutated CLN3, Juvenile Neuronal Ceroid Lipofuscinosis (JNCL), which is also known as juvenile Batten disease, or any other disease involving mutated CLN3, such as autophagic vacuolar myopathy and CLN3-associated nonsyndromic retinal degeneration.

As will be understood by those skilled in the art, the methods disclosed herein may be applied for detection and/or quantification of CLN3 in any suitable sample. Suitable samples include, but are not limited to, tissue samples, fluids, or any other suitable type of sample. For example, in some embodiments, the sample includes a brain sample. In one embodiment, preparing the brain sample includes cryo-grinding frozen brain samples and then re-suspending them in a detergent containing buffer in the presence of protease inhibitors. Next, the samples are reduced and alkylated, then loaded onto microcolumns where they are proteolytically digested and subsequently eluted and concentrated. Alternatively, as CLN3 is an integral membrane protein, in some embodiments, the sample include platelets or other blood cells. In such embodiments, the samples may be collected non-invasively, such as through drawing of blood. After the blood is drawn, the platelets or other blood cells may be prepared for analysis according to the methods disclosed herein.

Further provided herein are compounds for detecting and/or quantifying CLN3 in a sample. In some embodiments, the compounds include heavy isotope labeled CLN3 peptides. In some embodiments, the CLN3 peptides are C-terminal residue labeled peptides. In some embodiments, the C-terminal residue labeled peptides are tryptic peptides. In some embodiments, the C-terminal residue labeled peptides are peptides that undergo proteolytic digestion other than with trypsin. Suitable heavy isotopes include, but are not limited to, C, N, or any other heavy isotope suitable for labeling. For example, in some embodiments, the compound includes one or more of the isotope labeled compounds below:

| Peptide ID | | Sequence | Sequence ID |
|---|---|---|---|
| P1 | 113 | LLAPLGLFILLPYSPR 127 | SEQ ID NO: 1 (endogenous) |
|  | 113 | LLAPLGLFILLPYSP[$^{15}N_4$,$^{13}C_6$-R] 127 | SEQ ID NO: 6 |
|  | 113 | LLAPLGLFILLPYS[$^{15}N_4$,$^{13}C_5$-P]R 127 | SEQ ID NO: 7 |
|  | 113 | LLAPLGLFILLPYS[$^{15}N$,$^{13}C_5$-P][$^{15}N_4$,$^{13}C_6$-R] 127 | SEQ ID NO: 8 |
| P2 | 310 | NTSLSHAQQYR 320 | SEQ ID NO: 2 (endogenous) |
|  | 310 | NTSLSHAQQY[$^{15}N_4$,$^{13}C_6$-R] 320 | SEQ ID NO: 9 |
|  | 310 | NTSLSHAQQ[$^{15}N$,$^{13}C_9$-Y]R 320 | SEQ ID NO: 10 |
|  | 310 | NTSLSHAQQ[$^{15}N$,$^{13}C_9$-Y][$^{15}N_4$,$^{13}C_6$-R] 320 | SEQ ID NO: 11 |
| P3 | 17 | EETDSEPQAPR 27 | SEQ ID NO: 3 (endogenous) |
|  | 17 | EETDSEPQAP[$^{15}N_4$,$^{13}C_6$-R] 27 | SEQ ID NO: 12 |
|  | 17 | EETDSEPQA[$^{15}N$,$^{13}C_5$-P]R 27 | SEQ ID NO: 13 |
|  | 17 | EETDSEPQA[$^{15}N$,$^{13}C_5$-P][$^{15}N_4$,$^{13}C_6$-R] 27 | SEQ ID NO: 14 |
| P5 | 11 | FSDSEGEETVPEPR 24 | SEQ ID NO: 4 (endogenous) |
|  | 11 | FSDSEGEETVPEP[$^{15}N_4$,$^{13}C_6$-R] 24 | SEQ ID NO: 15 |
|  | 11 | FSDSEGEETVPEP[$^{13}C_6$-R] 24 | SEQ ID NO: 15 |
|  | 11 | FSDSEGEETVPE[$^{15}N$,$^{13}C_5$-P]R 24 | SEQ ID NO: 16 |
|  | 11 | FSDSEGEETVPE[$^{15}N$,$^{13}C_5$-P][$^{15}N_4$,$^{13}C_6$-R] 24 | SEQ ID NO: 17 |
| P7 | 256 | TEAPESKPGSSSSLSLR 272 | SEQ ID NO: 5 (endogenous) |
|  | 256 | TEAPESKPGSSSSLSL[$^{15}N_4$,$^{13}C_6$-R] 272 | SEQ ID NO: 18 |
|  | 256 | TEAPESKPGSSSSLS[$^{15}N$,$^{13}C_6$-L]R 272 | SEQ ID NO: 19 |
|  | 256 | TEAPESKPGSSSSLS[$^{15}N$,$^{13}C_6$-L][$^{15}N_4$,$^{13}C_6$-R] 272 | SEQ ID NO: 20 |

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

EXAMPLES

These Examples focus on the development of a mass spectrometry-based method to detect and quantify CLN3 protein. Specifically, proteolytic (e.g., tryptic) peptides of CLN3 that have good mass spectrometric responses and are unique to the proteome (human, mouse or any) were identified, these peptides were synthesized with the C-terminal 1-5 residue stable isotope labels, and a Parallel Reaction Monitoring (PRM) data acquisition method using a hybrid quadrupole-Orbitrap (q-OT) mass spectrometer (or a quadrupole time-of-flight (q-TOF) mass spectrometer) was developed. Accordingly, without wishing to be bound by theory, these Examples are believed to describe not only the first method to detect WT and mutant CLN3 proteins, but also the first method to quantify WT and mutant CLN3 proteins, which is notoriously difficult and of great medical importance.

Example 1—Development of Mass Spectrometry-Based Method

Peptide Selection

Seven tryptic peptides (P1-P7 as shown below) were initially chosen as the markers for WT human and/or mouse CLN3 proteins, as these are unique in human and/or mouse proteomes based on a bioinformatic analysis. These peptides were synthesized using solid phase peptide synthesis. Stable isotope-labeled amino acids (e.g., [$^{15}N_4$,$^{13}C_6$-R], [$^{15}N_2$,$^{13}C_6$-K], and [$^{13}C_6$-R]) were added during peptide synthesis so that the C-terminal 1-2 amino acid residues for each peptide was labeled (Table 1). The P4 peptide, which contains two cysteines, was synthesized by adding cysteines with carboxyamidomethylation as the endogenous peptide is alkylated with carboxyamidomethylation during sample preparation. While any heavy isotope may be used, either C or N was preferred on the last C-terminal residues (for trypsin digestion, K and R) so that all y ions (the ion series that is observed the most) are labeled with a heavy isotope. For other proteolytic digestion, corresponding last C-terminal residues can be labeled. Completely synthesized peptides were cleaved from resin and purified by reverse phase HPLC using acetonitrile/$H_2O$ and 0.1% (v/v) trifluoroacetic acid. Based on the amino acid analysis results, known quantities of purified peptides were aliquoted and lyophilized.

TABLE 1

Endogenous and corresponding stable isotope-labeled tryptic peptides tested for CLN3 protein detection and absolute quantification. n.d., not determined (P4 and P6 were excluded from the final list of selected standard peptides).

| Peptide ID | Good for detecting CLN3 Human WT | Good for detecting CLN3 Human 1 kb | Good for detecting CLN3 Mouse WT | Good for detecting CLN3 Mouse 1 kb | Sequences of endogenous peptides and heavy isotope labeled peptide standards | Visible in Mass Spec | Detected in human cells | Detected in mouse cells | Linear response |
|---|---|---|---|---|---|---|---|---|---|
| P1 | ✓ | ✓ | ✓ | ✓ | 113 LLAPLGLHLLPYSPR 127<br>113 LLAPLGLHLLPYSP[$^{15}N_4$,$^{13}C_6$-R] 127<br>113 LLAPLGLHLLPYS[$^{15}N$,$^{13}C_5$-P]R 127<br>113 LLAPLGLHLLPYS[$^{15}N$,$^{13}C_5$-P][$^{15}N_4$,$^{13}C_6$-R] 127 | Yes | Yes | Yes | Yes |
| P2 | | | ✓ | | 310 NTSLSHAQQYR 320<br>310 NTSLSHAQQY[$^{15}N_4$,$^{13}C_6$-R] 320<br>310 NTSLSHAQQ[$^{15}N$,$^{13}C_9$-Y]R 320<br>310 NTSLSHAQQ[$^{15}N$,$^{13}C_9$-Y][$^{15}N_4$,$^{13}C_6$-R] 320 | Yes | No | Yes | Yes |
| P3 | | | ✓ | ✓ | 17 EETDSEPQAPR 27<br>17 EETDSEPQAP[$^{15}N_4$,$^{13}C_6$-R] 27<br>17 EETDSEPQA[$^{15}N$,$^{13}C_5$-P]R 27<br>17 EETDSEPQA[$^{15}N$,$^{13}C_5$-P][$^{15}N_4$,$^{13}C_6$-R] 27 | Yes | n.d. | — | n.d. |
| P4 (not selected) | | | ✓ | | 335 SSLQCCR 341<br>335 SSLQCamCam[$^{15}N_4$,$^{13}C_6$-R] 341 | Yes | n.d. | — | n.d. |
| P5 | ✓ | ✓ | | | 11 FSDSEGEETVPEPR 24<br>11 FSDSEGEETVPEP[$^{15}N_4$,$^{13}C_6$-R] 24<br>11 FSDSEGEETVPEP[$^{13}C_6$-R] 24<br>11 FSDSEGEETVPE[$^{15}N$,$^{13}C_5$-P]R 24 | Yes | Yes | n.d. | Yes |
| P6 (not selected) | ✓ | ✓ | | | 25 LPLLDHQGAHWK 36<br>25 LPLLDHQGAHW[$^{15}N_2$,$^{13}C_6$-K] 36 | Yes | Yes | n.d. | No |
| P7 | ✓ | | | | 256 TEAPESKPGSSSSLSLR 272<br>256 TEAPESKPGSSSSLSL[$^{15}N_4$,$^{13}C_6$-R] 272<br>256 TEAPESKPGSSSSLS[$^{15}N$,$^{13}C_6$-L]R 272<br>256 TEAPESKPGSSSSLS[$^{15}N$,$^{13}C_6$-L][$^{15}N_4$,$^{13}C_6$-R] 272 | Yes | Yes | n.d. | Yes |

TABLE 2

The m/z values for stable isotope-labeled CLN3 tryptic peptides.

| Peptide ID | M (unlabeled) | Sequence | | | m/z (z = 1) | m/z (z = 2) | m/z (z = 3) |
|---|---|---|---|---|---|---|---|
| P1 | 1658.9872 | 113 | LLAPLGLHLLPYSP[$^{15}$N$_4$,$^{13}$C$_6$-R] | 127 | 1670.0027 | 835.5050 | 557.3391 |
|    |           | 113 | LLAPLGLHLLPYS[$^{15}$N,$^{13}$C$_5$-P]R | 127 | 1666.0078 | 833.5076 | 556.0075 |
|    |           | 113 | LLAPLGLHLLPYS[$^{15}$N,$^{13}$C$_5$-13][$^{15}$N$_4$,$^{13}$C$_6$-R] | 127 | 1676.0165 | 838.5119 | 559.3437 |
| P2 | 1303.6270 | 310 | NTSLSHAQQY[$^{15}$N$_4$,$^{13}$C$_6$-12] | 320 | 1314.6425 | 657.8249 | 438.8857 |
|    |           | 310 | NTSLSHAQQ[$^{15}$N,$^{13}$C$_9$-Y]R | 320 | 1314.6614 | 657.8343 | 438.8920 |
|    |           | 310 | NTSLSHAQQ[$^{15}$N,$^{13}$C$_9$-Y][$^{15}$N$_4$,$^{13}$C$_6$-R] | 320 | 1324.6697 | 662.8385 | 442.2281 |
| P3 | 1257.5474 | 17 | EETDSEPQAP[$^{15}$N$_4$,$^{13}$C$_6$-R] | 27 | 1268.5629 | 634.7851 | 423.5258 |
|    |           | 17 | EETDSEPQA[$^{15}$N,$^{13}$C$_5$-P]R | 27 | 1264.5684 | 632.7878 | 422.1943 |
|    |           | 17 | EETDSEPQA[$^{15}$N,$^{13}$C$_5$-P][$^{15}$N$_4$,$^{13}$C$_6$-R] | 27 | 1274.5766 | 637.7920 | 425.5304 |
| P4 | 909.3797 | 335 | SSLQCamCam[$^{15}$N$_4$,$^{13}$C$_6$-R] | 341 | 919.3881 | 460.7014 | 307.4700 |
| P5 | 1577.6846 | 11 | FSDSEGEETVPEP[$^{15}$N$_4$,$^{13}$C$_6$-R] | 24 | 1588.7001 | 794.8537 | 530.2382 |
|    |           | 11 | FSDSEGEETVPEP[$^{13}$C$_6$-R] | 24 | 1584.7120 | 792.8596 | 528.9088 |
|    |           | 11 | FSDSEGEETVPE[$^{15}$N,$^{13}$C$_5$-P]R | 24 | 1584.7056 | 792.8560 | 528.9067 |
|    |           | 11 | FSDSEGEETVPE[15N,13C5-P][15N4,13C6-R] | 24 | 1594.7139 | 797.8606 | 532.2428 |
| P6 | 1413.75176 | 25 | LPLLDHQGAHW[$^{15}$N$_2$,$^{13}$C$_6$-K] | 36 | 1421.7662 | 711.8904 | 474.9294 |
| P7 | 1731.86395 | 256 | TEAPESKPGSSSSLSL[$^{15}$N$_4$,$^{13}$C$_6$-R] | 272 | 1742.8795 | 871.9434 | 581.6313 |
|    |           | 256 | TEAPESKPGSSSSLS[$^{15}$N,$^{13}$C$_6$-L]R | 272 | 1738.8913 | 869.9493 | 580.3020 |
|    |           | 256 | TEAPESKPGSSSSLS[$^{15}$N,$^{13}$C$_6$-L][$^{15}$N$_4$,$^{13}$C$_6$-R] | 272 | 1748.8996 | 874.9534 | 583.6380 |

Figure 11:
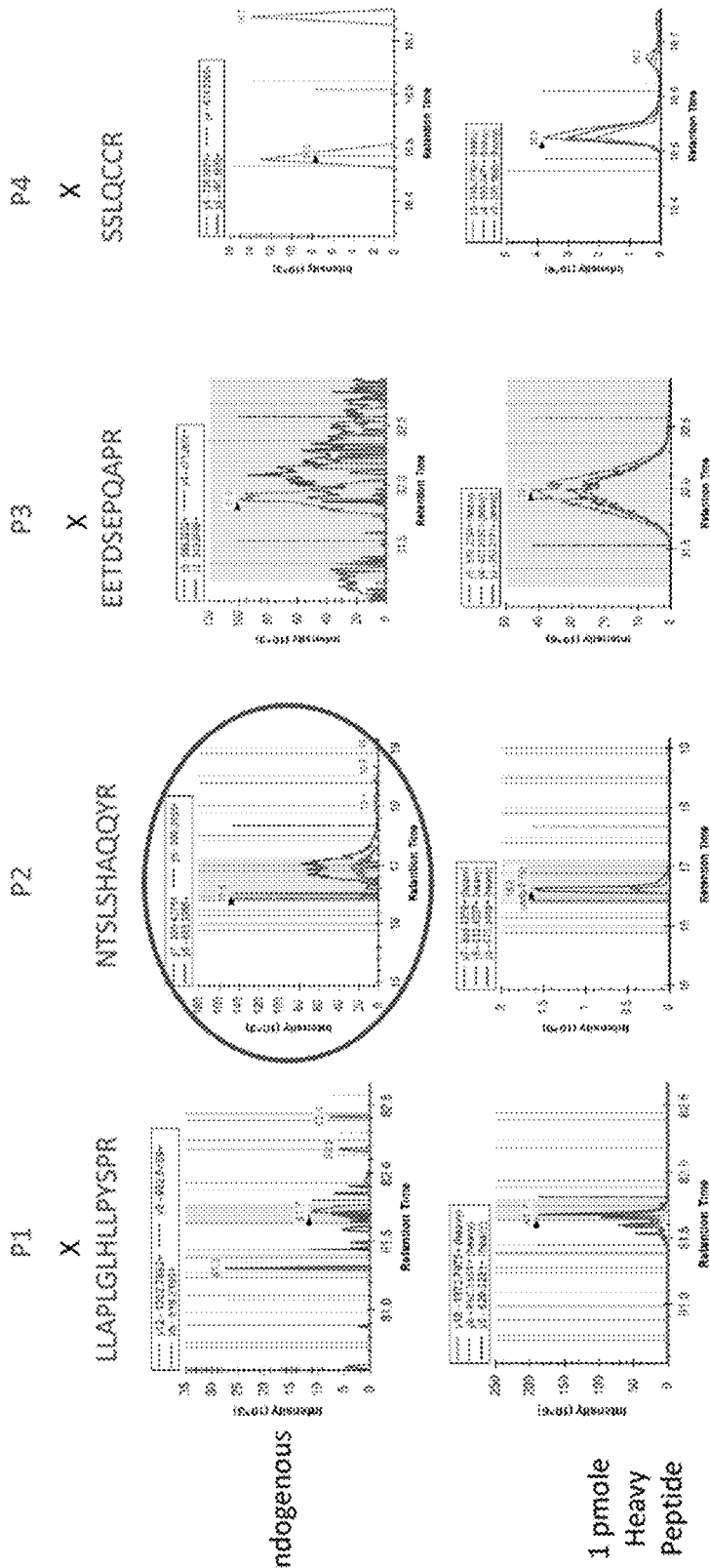
Figure 12:
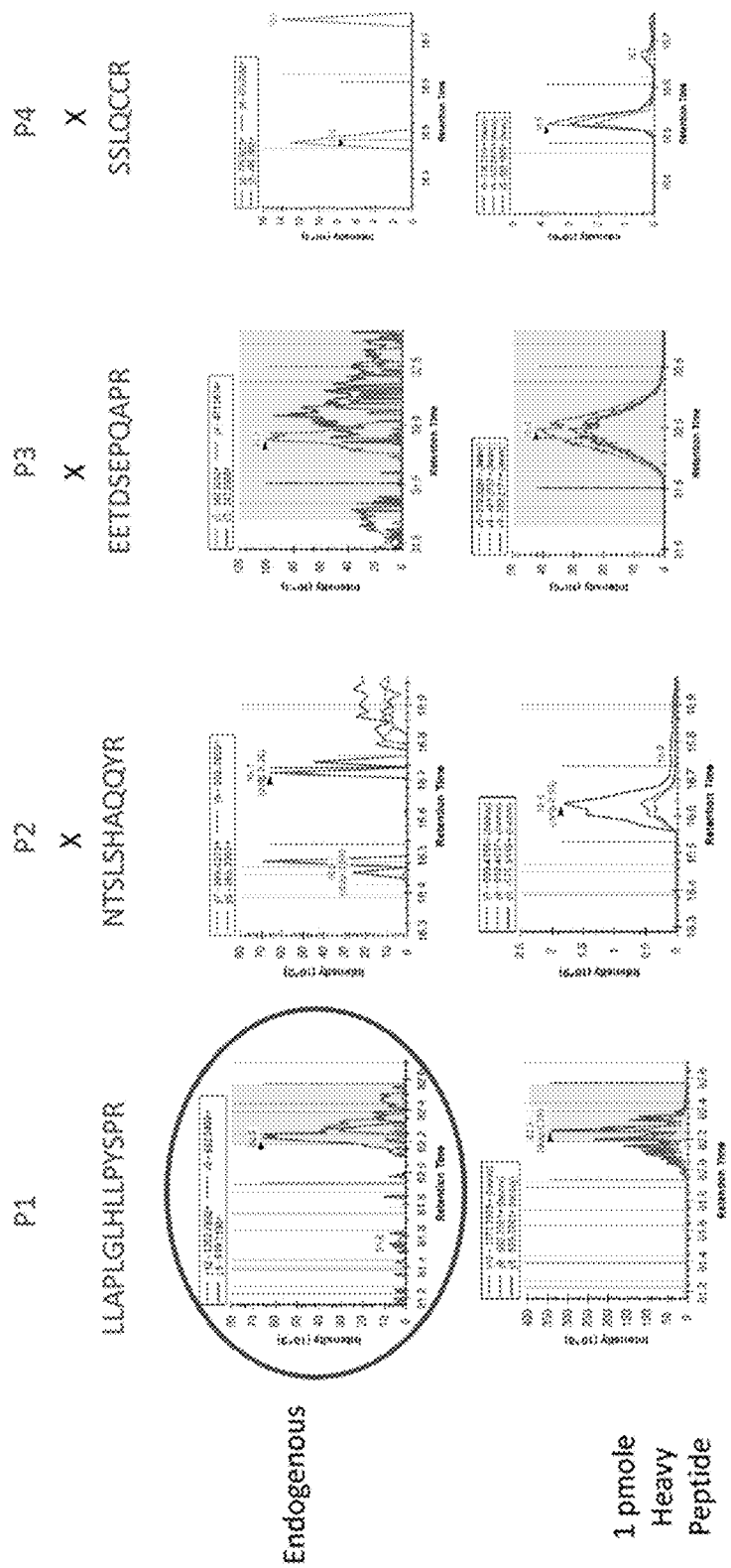

All of the 8 synthesized heavy isotope-labeled CLN3 tryptic peptides were visible in mass spectrometry (FIG. 1). Additionally, endogenous CLN3 tryptic peptides corresponding to P1, P2, P5/P5', P6, P7 were detected in human (FIGS. 2-9) and mouse (FIGS. 10-12) cell lines. However, it is noted that among the 7 chosen CLN3 peptides, some peptides were below the detection limit in some cell lines. Without wishing to be bound by theory, it is believed that certain peptides were undetectable due to different cell-specific posttranslational modifications on these peptides.

Unlabeled Protein Detection

The parallel reaction monitoring (PRM) data acquisition method uses a hybrid quadrupole-Orbitrap (q-OT) mass spectrometer or a quadrupole time-of-flight (q-TOF) mass spectrometer to detect and quantify corresponding unlabeled CLN3 peptides in the samples spiked with known amounts of heavy isotope labeled standards (which were carefully titrated in order to better quantify the amounts of endogenous CLN3 peptides). The unlabeled CLN3 peptides in the samples have the same elution times as corresponding labeled peptides. The elution times for a given separation column, flow rate and gradient were first determined using the heavy isotope labeled standards, and this retention time information was then used for targeted scheduled PRM events for both the heavy isotope labeled and endogenous unlabeled peptides. Both the unlabeled and heavy isotope labeled CLN3 peptides at the determined elution times were analyzed by an Orbitrap mass spectrometer coupled to an LC system.

This CLN3 protein quantification method may be applied on several studies, including determining CLN3 protein levels in cell lines and animal models (e.g., mouse, dog, sheep, pig, bovine, and zebrafish) with CLN3 gene knockdown and knockout, in cancer cells with CLN3 overexpression, in various mouse and human tissues and body fluids (e.g., blood and saliva swaps for non-invasive testing; see Example 3), in various developmental stages, in young and old ages, in males and females, in patients with CLN3 mutations; and in patients that have undergone treatments (e.g., those enrolled in CLN3 gene therapy and BBDF101 small molecular therapy clinical trials). This method also applies to studies that determine subcellular distribution of WT and mutant CLN3 proteins, when coupled with subcellular fractionation or imaging mass spectrometry. Additionally, an analogous strategy will work for other CLN3 proteolytic peptides digested by proeolytic enzymes other than trypsin and for the Selected Reaction Monitoring (SRM) data acquisition method using a triple-quadrupole (QQQ) or a hybrid quadrupole-linear ion trap (QTrap) mass spectrometer.

Example 2—Determination of Mutant Protein Levels

Majority of juvenile Batten disease patients are homozygous of a 1 kb-deletion mutation in the CLN3 gene, which presumably leads to a shorter protein with the first 153 amino acids the same as the WT CLN3 protein followed by additional new C-terminal 28 amino acids, if this mutant protein is ever expressed. As peptides P1, P5/P5' and P6 are at the N-terminal part of human CLN3 (P1 and P3 for mouse CLN3), these peptides are retained in the 1 kb mutant (Table 1). Therefore, the residual levels of the 1 kb mutant protein can be quantified in patients with homozygous 1 kb-deletion mutation by monitoring these peptides in patient samples. In contrast, peptide P7 is at the C-terminal part of human CLN3 (P2 and P4 for mouse CLN3). Thus, the amounts of WT and 1 kb mutant proteins can be quantified in heterozygous samples by comparing the amounts detected by P1, P5/P5', and P6 versus by P2 and P7.

For homozygous patients with other known point mutations, the mutant proteins can be quantified using the same heavy isotope labeled standards. Even if a mutation occurs within one of the 7 peptides, the mutant protein can be quantified by heavy versions of the other 6 peptides. Alternatively, additional heavy point mutant peptides can be synthesized to directly quantify point mutant protein. For heterozygous patients with one copy of 1 kb deletion and one copy of other known point mutations, if the point mutation occurs within one of the 7 peptides, the amounts detected by P1, P5/P5', or P6 can be compared to the amounts detected by P2 or P7 to determine the amounts of 1 kb deletion mutant protein and the point mutant protein, as long as the peptide containing the point mutation is excluded from the analysis. Alternatively, heavy point mutant peptides can be synthesized to directly quantify point mutant protein.

Example 3—Detection of CLN3 Peptides in Mouse and Human Samples

Figure 13:
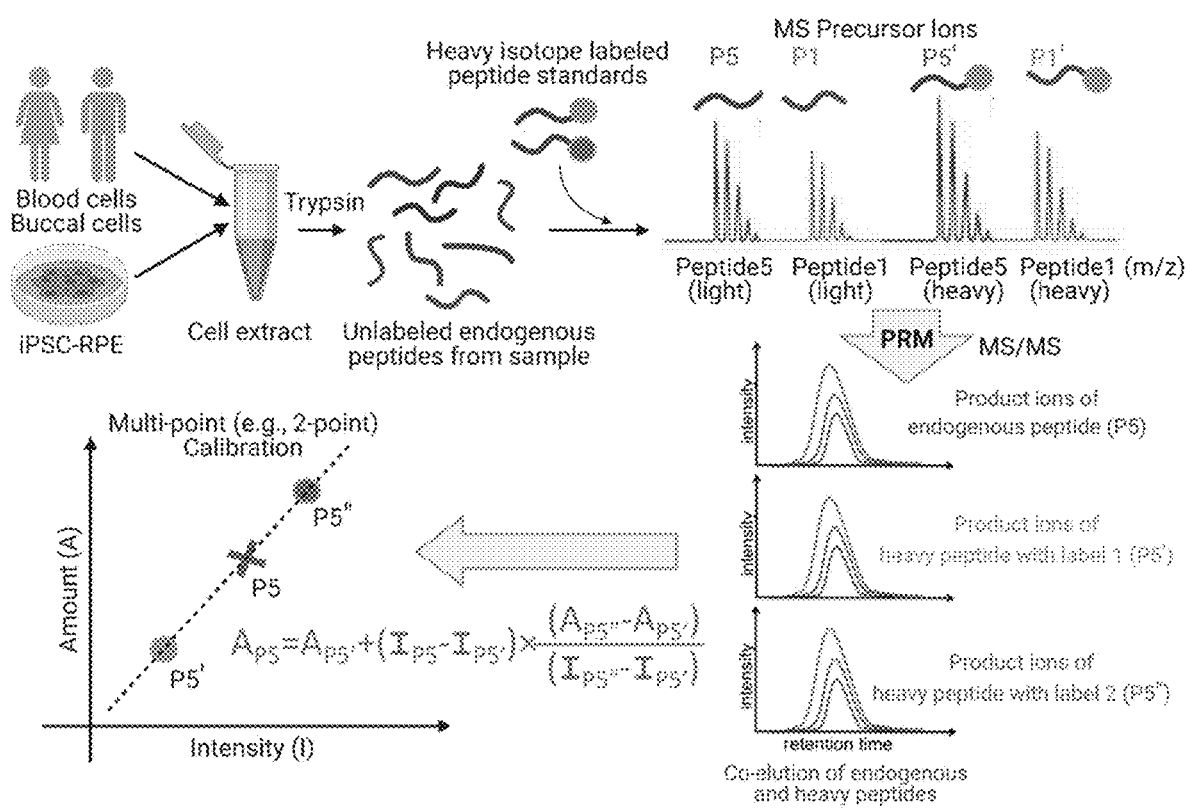
FIG. 13 shows a schematic illustrating a method of detecting and quantifying CLN3 proteins.
Figure 14A:
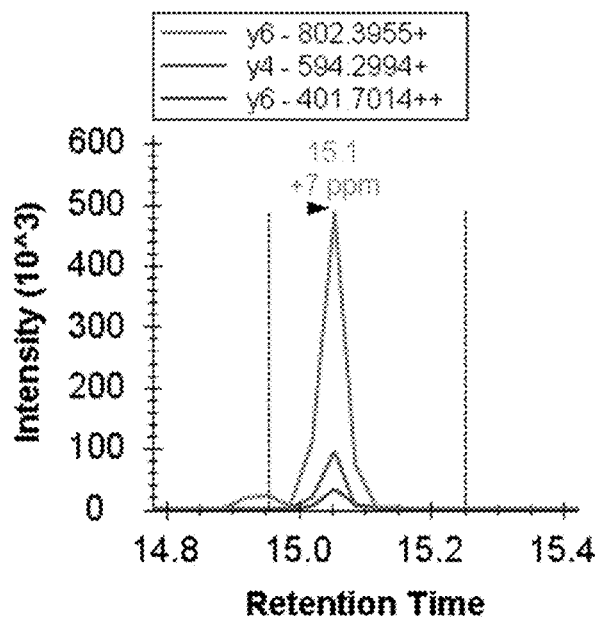
FIGS. 14A-B show graphs illustrating the CLN3 tryptic peptides were detected in mouse brain lysates. (A) Endogenous P2 peptides. (B) Spiked heavy P2 peptides. Each mouse brain sample (1 µg total proteins) was spiked with heavy peptides (100 fmol each). Data were acquired by PRM on an Easy nLC 1200 connected to a Q Exactive HF-X Orbitrap mass spectrometer. P2: NTSLSHAQQYR (SEQ ID NO: 2).
Figure 14B:
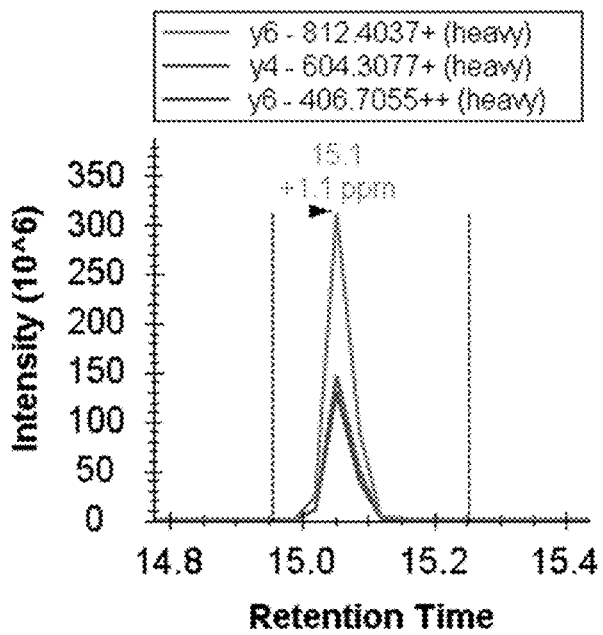
Figure 15A:
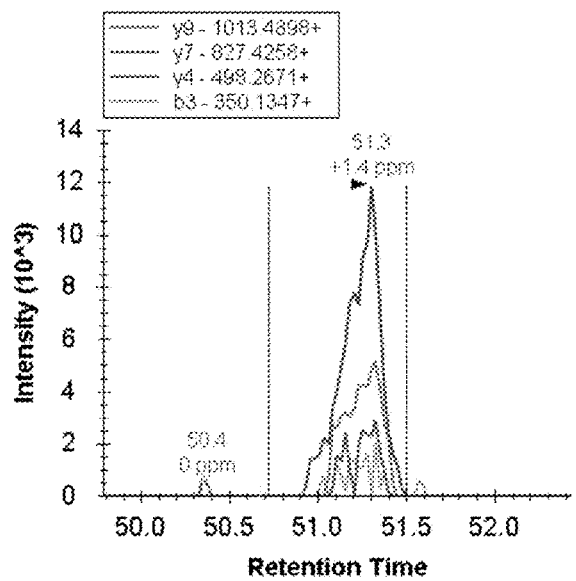
FIGS. 15A-D show graphs illustrating the CLN3 tryptic peptides were detected in human cerebrum protein lysates. (A) Endogenous P5 peptides. (B) Spiked heavy P5 peptides. (C) Endogenous P7 peptides. (D) Spiked heavy P7 peptides. Each human cerebellum sample (2 g total proteins) was spiked with heavy peptides (500 fmol each). Data were acquired by PRM on an Easy nLC 1200 connected to a Q Exactive HF-X Orbitrap mass spectrometer. P5: FSDSEGEETVPEPR (SEQ ID NO: 5); P7 TEAPESKPGSSSSLSLR (SEQ ID NO: 7).
Figure 15B:
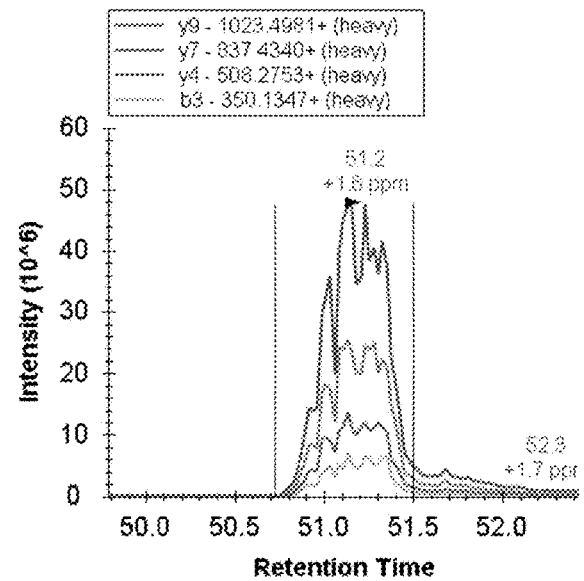
Figure 15C:
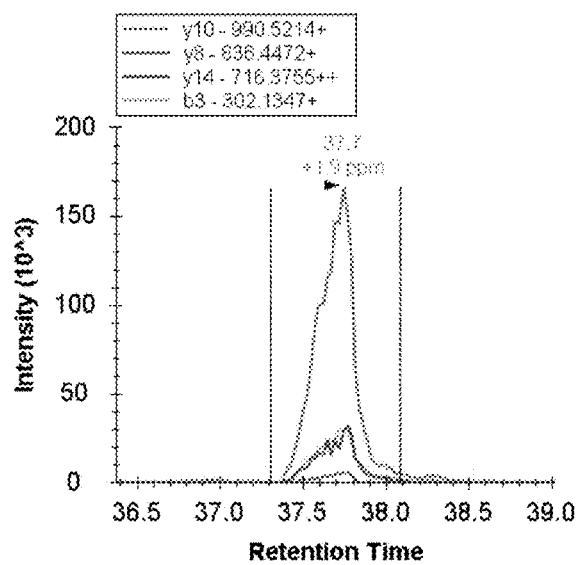
Figure 15D:
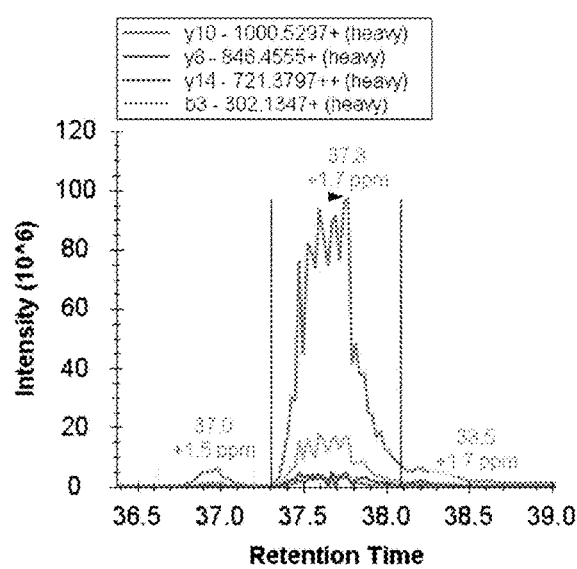
Figure 16A:
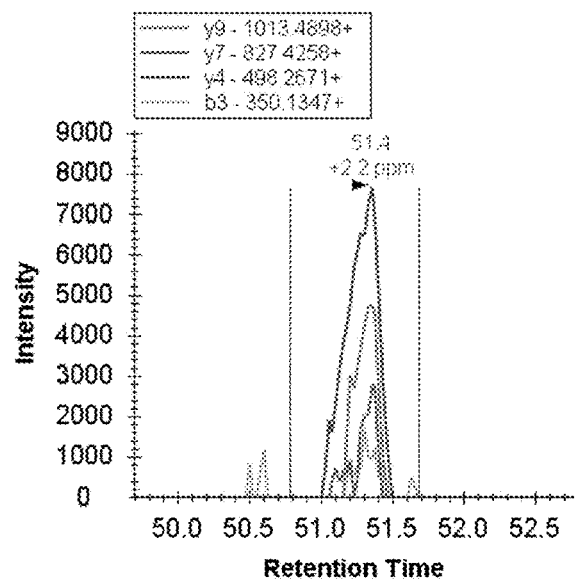
FIGS. 16A-D show graphs illustrating the CLN3 tryptic peptides were detected in freshly isolated human platelets. (A) Endogenous P5 peptides. (B) Spiked heavy P5 peptides. (C) Endogenous P7 peptides. (D) Spiked heavy P7 peptides. Each human platelet sample (2 µg total proteins) was spiked with heavy peptides (500 fmol each). Data were acquired by PRM on an Easy nLC 1200 connected to a Q Exactive HF-X Orbitrap mass spectrometer. P5: FSDSEGEETVPEPR (SEQ ID NO: 5); P7: TEAPESKPGSSSSLSLR (SEQ ID NO: 7).
Figure 16B:
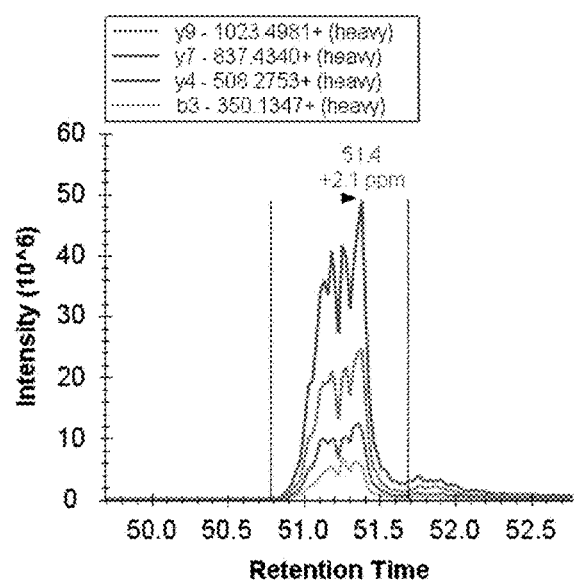
Figure 16C:
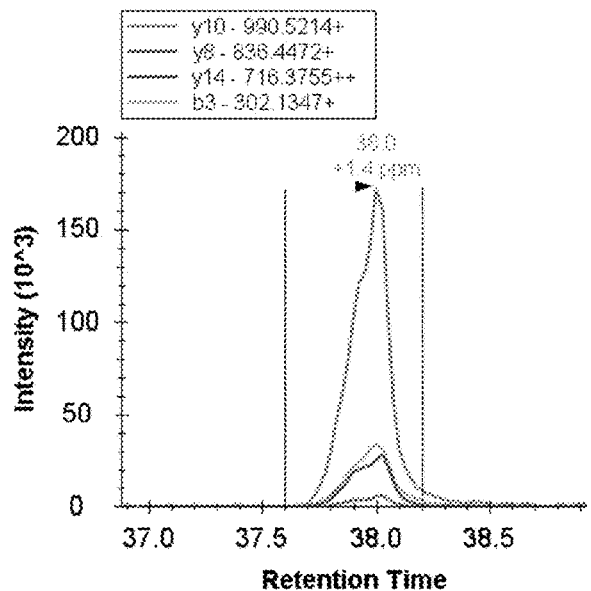
Figure 16D:
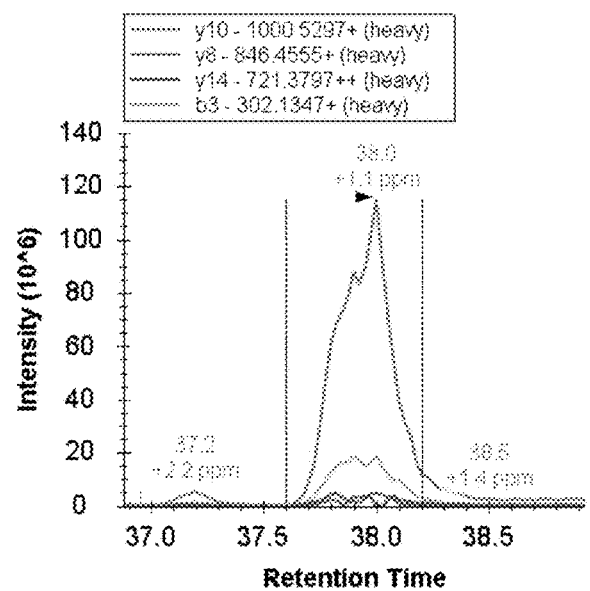
Figure 17A:
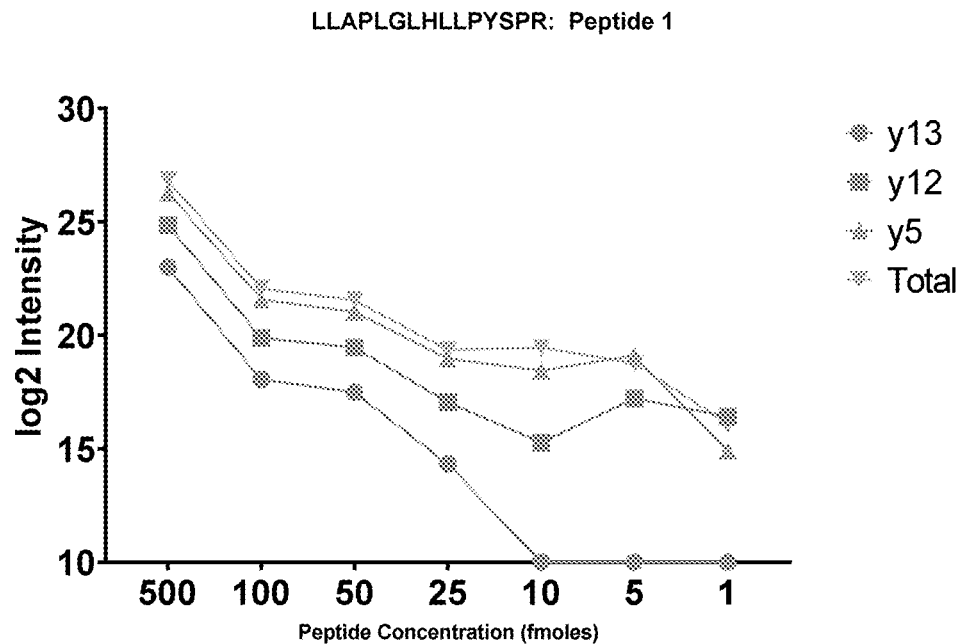
FIGS. 17A-E show graphs illustrating limit of detection of heavy isotope labeled CLN3 peptides in human brain samples. (A) Peptide 1 (P1) showed linear responses. (B) Peptide 2 (P2) showed linear responses. (C) Peptide 5 (P5)
Figure 17B:
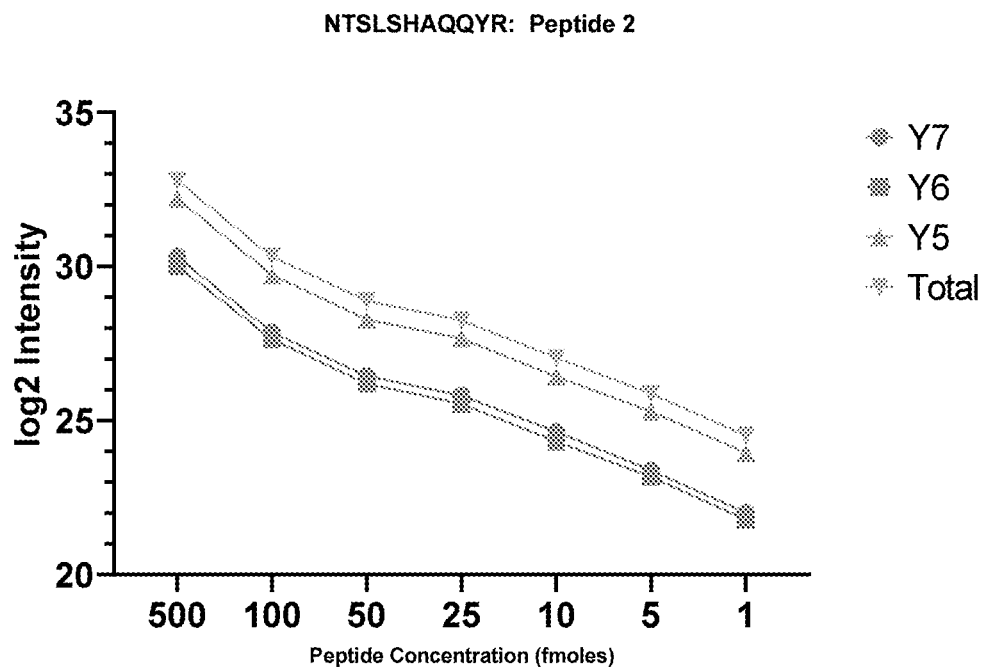
Figure 17C:
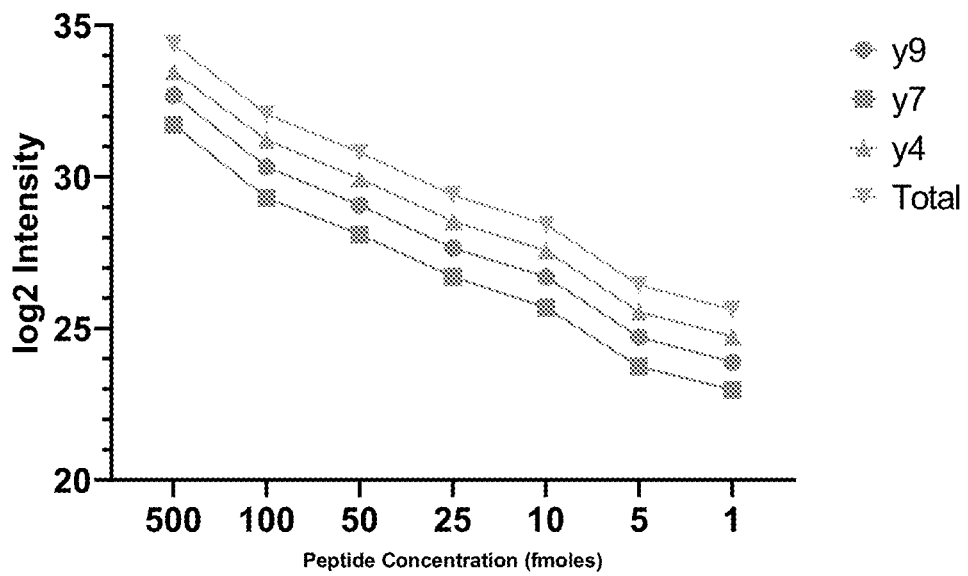
Figure 17D:
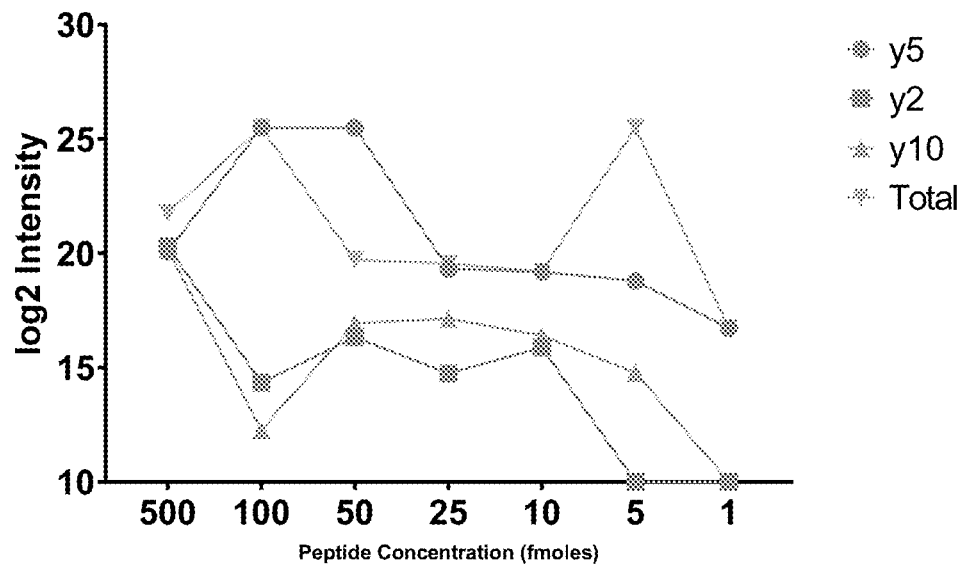
Figure 17E:
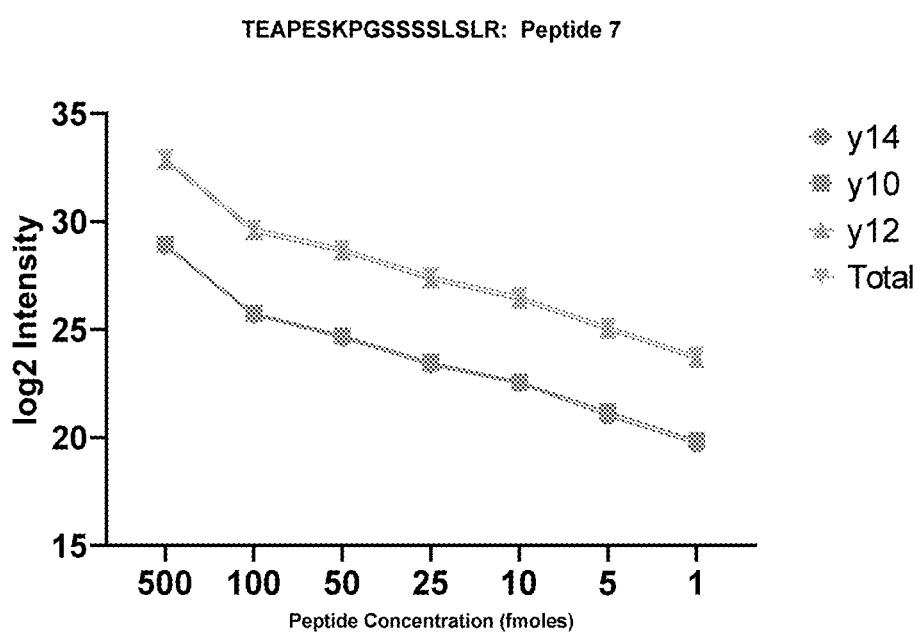

An overview of a method of quantifying CLN3 protein in a sample using 2-point calibration is shown in FIG. 13. Using the detection and quantification method above, CLN3 tryptic peptides were evaluated in mouse and human samples. FIGS. 14A-B show the detection of endogenous and spiked heavy P2 peptides in mouse brain lysates. FIGS. 15A-D show the detection of endogenous and spiked heavy P5 (FIGS. 15A-B) and P7 (FIGS. 15C-D) peptides in human cerebrum protein lysates. FIGS. 16A-D show the detection of endogenous and spiked heavy P5 (FIGS. 16A-B) and P7 (FIGS. 16C-D) peptides in freshly isolated human platelets.

Example 4—Quantification of CLN3 Peptides in Mouse and Human Samples

FIGS. 17A-E show limit of detection results in human brain samples, where peptides P1, P2, P5, and P7 showed linear responses, P6 did not show linear response, and P4 was hard to detect. Therefore, we recommend optimal heavy peptide standard list to include P1, P2, P3, P5 and P7. We synthesized 3 versions of heavy peptides for each of these peptides (Table 1). The 3 versions of heavy peptides (50 amol, 500 amol, and 5 fmol, respectively) will be spiked into mouse and human samples (2 μg total protein per sample) and quantified as described above in Example 3.

Example 5—Sample Preparation and Analysis

Frozen brain samples are cryo-ground in liquid nitrogen and resuspended in a detergent-containing buffer (e.g., 5% SDS in 100 mM Ammonium bicarbonate pH 8.0) in the presence of protease inhibitors. Samples are then reduced (e.g., with dithiothreitol) and alkylated (e.g., with iodoacetamide). Each sample is loaded onto S-Trap microcolumns (Protifi, USA) according to the manufacturer's instructions. On-column proteolytic digestion is performed and peptides are eluted using 40% acetonitrile in 0.5% acetic acid, followed by 80% acetonitrile in 0.5% acetic acid, and concentrated in a SpeedVac.

LC run is carried out, for example, with an EASY-Spray analytical column with solvent A (2% acetonitrile in 0.5% acetic acid) and solvent B (80% acetonitrile in 0.5% acetic acid). Peptides are eluted into an Orbitrap QExactive HF-X Mass Spectrometer (Thermo Fisher Scientific) by using the following gradient: 5-15% in 40 min, 16-40% in 15 min, followed by 40-100% in 15 min. High resolution full MS spectra were recorded at a resolution of 45,000, an AGC target of 3e6, a maximum ion time of 45 ms, and a scan range from 400 to 2000 m/z. Following each full MS scan, parallel reaction monitoring (PRM) scans were acquired for the peptides of interest. MS/MS spectra were collected at a resolution of 30,000, an AGC target of 2e5, maximum ion time of 120 ms, one microscan, 0.7 m/z isolation window, fixed first mass of 150 m/z, dynamic exclusion of 30 sec, and Normalized Collision Energy (NCE) of 27.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Nelson, T., D. A. Pearce, and A. D. Kovacs, Lack of specificity of antibodies raised against CLN3, the lysosomal/endosomal transmembrane protein mutated in juvenile Batten disease. Biosci Rep, 2017. 37(6).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

---

What is claimed is:

1. A compound for detecting CLN3 in a sample, the compound comprising a heavy isotope labeled CLN3 proteotypic peptide.

2. The compound of claim 1, wherein the peptide is a tryptic peptide.

3. The compound of claim 2, wherein the heavy isotope is C or N.

4. The compound of claim 1, wherein the heavy isotope label is applied to a C-terminal residue of the peptide.

5. The compound of claim 4, wherein the heavy isotope label is applied to at least one of the final two C-terminus residues of the peptide.

6. The compound of claim 4, wherein the C-terminus residue is at least one of K and R.

7. The compound of claim 4, wherein the heavy isotope labeled residue is $^{15}N_4,^{13}C_6$-R; $^{15}N_2,^{13}C_6$-K; $^{15}N,^{13}C_5$-P; $^{15}N,^{13}C_9$-Y; $^{15}N,^{13}C_6$-L; or $^{13}C_6$-R.

8. The compound of claim 1, wherein the compound is selected from the group consisting of 113 LLAPLGLHLLPYSP[$^{15}N_4,^{13}C_6$-R] 127 (SEQ ID NO: 6), 113 LLAPLGLHLLPYS[$^{15}N,^{13}C_5$-P]R 127 (SEQ ID NO: 7), 113 LLAPLGLHLLPYS[$^{15}N,^{13}C_5$-P][$^{15}N_4,^{13}C_6$-R] 127 (SEQ ID NO: 8), 310 NTSLSHAQQY[$^{15}N_4,^{13}C_6$-R] 320 (SEQ ID NO: 9), 310 NTSLSHAQQ[$^{15}N,^{13}C_9$-Y]R 320 (SEQ ID NO: 10), 310 NTSLSHAQQ[$^{15}N,^{13}C_9$-Y][$^{15}N_4,^{13}C_6$-R] 320 (SEQ ID NO: 11), 17 EETDSEPQAP[$^{15}N_4,^{13}C_6$-R] 27 (SEQ ID NO: 12), 17 EETDSEPQA[$^{15}N,^{13}C_5$-P]R 27 (SEQ ID NO: 13), 17 EETDSEPQA[$^{15}N,^{13}C_5$-P][$^{15}N_4,^{13}C_6$-R] 27 (SEQ ID NO: 14), 11 FSDSEGEETVPEP[$^{15}N_4,^{13}C_6$-R] 24 (SEQ ID NO: 15), 11 FSDSEGEETVPEP[$^{13}C_6$-R] 24 (SEQ ID NO: 15), 11 FSDSEGEETVPE[$^{15}N,^{13}C_5$-P]R 24 (SEQ ID NO: 16), 11 FSDSEGEETVPE[$^{15}N,^{13}C_5$-P][$^{15}N_4,^{13}C_6$-R] 24 (SEQ ID NO: 17), 256 TEAPESKPGSSSSLSL[$^{15}N_4,^{13}C_6$-R] 272 (SEQ ID NO: 18), 256 TEAPESKPGSSSSLS[$^{1}N,^{13}C_6$-L]R 272 (SEQ ID NO: 19), 256 TEAPESKPGSSSSLS[$^{15}N,^{13}C_6$-L][$^{15}N_4,^{13}C_6$-R] 272 (SEQ ID NO: 20), and combinations thereof.

9. A method for detecting CLN3, the method comprising:
i) selecting a CLN3 proteotypic peptide that exhibits linear behavior in the mass spectrometer;
ii) generating a stable isotope labeled standard;
iii) spiking known amounts of the stable isotope labeled standard into a sample to form a spiked sample;
iv) determining retention times and establishing calibration curves using the spiked sample; and
v) detecting unlabeled selected CLN3 proteins in the sample.

10. The method of claim 9, wherein the CLN3 proteotypic peptide is unique in mouse, human, or other proteomes.

11. The method of claim 9, wherein the proteotypic peptide is a tryptic peptide.

12. The method of claim 9, wherein the stable isotope labeled standard comprises a compound according to claim 1.

13. The method of claim 9, wherein establishing calibration curves comprises determining at least one of a lower limit of detection, a linear detection range, and LC-MS parameters.

14. The method of claim 9, wherein detecting the unlabeled selected CLN3 proteins in the sample comprises:
mixing a known concentration of the isotope labeled standard into a sample;
eluting the peptides from the sample; and
determining whether the isotope labeled standard co-elutes with an unlabeled proteotypic peptide from the unlabeled selected CLN3 proteins.

15. The method of claim 14, further comprising quantifying the unlabeled selected CLN3 proteins in the sample.

16. The method of claim 15, wherein quantifying the unlabeled selected CLN3 proteins comprises calculating the amount of unlabeled proteotypic peptide based on the intensity of the corresponding isotope labeled standard of known concentration.

17. The method of claim 14, further comprising:
mixing a known concentration of an additional isotope labeled standard into the sample, the additional isotope labeled standard corresponding to a protein that is present in wild-type CLN3 but not mutated CLN3;
eluting the peptides from the sample;
determining whether the eluted peptides include an unlabeled proteotypic peptide from the unlabeled selected CLN3 protein that co-elutes with the isotope labeled standard; and
determining whether the detected peptides include mutated CLN3 protein using the additional isotope labeled standard.

18. The method of claim 9, wherein:
the unlabeled selected CLN3 proteins are mutant proteins;
generating the stable isotope labeled standard includes generating a heavy isotope labeled mutant peptide; and
detecting the unlabeled selected mutant CLN3 proteins in the sample comprises mixing a known concentration of the heavy isotope labeled mutant peptide into the sample; eluting the peptides from the sample; and determining whether the heavy isotope labeled mutant peptide co-elutes with an unlabeled proteotypic peptide from the unlabeled selected mutant CLN3 proteins.

19. The method of claim 9, wherein the method is non-invasive and the sample comprises platelets isolated from a subjects blood.

20. The method of claim 9, further comprising determining whether a subject has a disease based upon the amount of CLN3 protein expressed or the presence of a mutated CLN3.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Artificial Sequence
<220> FEATURE:
<223> OTHER INFORMATION: CLN3 peptide 1

<400> SEQUENCE: 1

Leu Leu Ala Pro Leu Gly Leu His Leu Leu Pro Tyr Ser Pro Arg
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: CLN3 peptide 2
```

<400> SEQUENCE: 2

Asn Thr Ser Leu Ser His Ala Gln Gln Tyr Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: CLN3 peptide 3

<400> SEQUENCE: 3

Glu Glu Thr Asp Ser Glu Pro Gln Ala Pro Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: CLN3 peptide 5

<400> SEQUENCE: 4

Phe Ser Asp Ser Glu Gly Glu Glu Thr Val Pro Glu Pro Arg
1               5                   10

<210> SEQ ID NO 5
<211> LENGTH: 17
<212> TYPE: PRT
<213> ORGANISM: Artificial Sequence
<220> FEATURE:
<223> OTHER INFORMATION: CLN3 peptide 7

<400> SEQUENCE: 5

Thr Glu Ala Pro Glu Ser Lys Pro Gly Ser Ser Ser Leu Ser Leu
1               5                   10                  15

Arg

<210> SEQ ID NO 6
<211> LENGTH: 15
<212> TYPE: PRT
<213> ORGANISM: Artificial Sequence
<220> FEATURE:
<223> OTHER INFORMATION: Isotope-labeled CLN3 peptide 1
<220> FEATURE:
<221> NAME/KEY: MISC_FEATURE
<222> LOCATION: (15)..(15)
<223> OTHER INFORMATION: Isotope label

<400> SEQUENCE: 6

Leu Leu Ala Pro Leu Gly Leu His Leu Leu Pro Tyr Ser Pro Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Isotope labeled CLN3 peptide 1
<220> FEATURE:
<221> NAME/KEY: MISC_FEATURE
<222> LOCATION: (14)..(14)
<223> OTHER INFORMATION: Isotope label

<400> SEQUENCE: 7

Leu Leu Ala Pro Leu Gly Leu His Leu Leu Pro Tyr Ser Pro Arg

<210> SEQ ID NO 8
<211> LENGTH: 15
<212> TYPE: PRT
<213> ORGANISM: Artificial Sequence
<220> FEATURE:
<223> OTHER INFORMATION: Isotope labeled CLN3 peptide 1
<220> FEATURE:
<221> NAME/KEY: MISC_FEATURE
<222> LOCATION: (14)..(14)
<223> OTHER INFORMATION: Isotope label
<220> FEATURE:
<221> NAME/KEY: MISC_FEATURE
<222> LOCATION: (15)..(15)
<223> OTHER INFORMATION: Isotope label

<400> SEQUENCE: 8

Leu Leu Ala Pro Leu Gly Leu His Leu Leu Pro Tyr Ser Pro Arg
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Isotope-labeled CLN3 peptide 2
<220> FEATURE:
<221> NAME/KEY: MISC_FEATURE
<222> LOCATION: (11)..(11)
<223> OTHER INFORMATION: Isotope label

<400> SEQUENCE: 9

Asn Thr Ser Leu Ser His Ala Gln Gln Tyr Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Isotope labeled CLN3 peptide 2
<220> FEATURE:
<221> NAME/KEY: MISC_FEATURE
<222> LOCATION: (10)..(10)
<223> OTHER INFORMATION: Isotope label

<400> SEQUENCE: 10

Asn Thr Ser Leu Ser His Ala Gln Gln Tyr Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Isotope labeled CLN3 peptide 2
<220> FEATURE:
<221> NAME/KEY: MISC_FEATURE
<222> LOCATION: (10)..(10)
<223> OTHER INFORMATION: Isotope label
<220> FEATURE:
<221> NAME/KEY: MISC_FEATURE
<222> LOCATION: (11)..(11)
<223> OTHER INFORMATION: Isotope label

<400> SEQUENCE: 11

Asn Thr Ser Leu Ser His Ala Gln Gln Tyr Arg
1               5                   10

```
<210> SEQ ID NO 12
<211> LENGTH: 11
<212> TYPE: PRT
<213> ORGANISM: Artificial Sequence
<220> FEATURE:
<223> OTHER INFORMATION: Isotope labeled CLN3 peptide 3
<220> FEATURE:
<221> NAME/KEY: MISC_FEATURE
<222> LOCATION: (11)..(11)
<223> OTHER INFORMATION: Isotope label

<400> SEQUENCE: 12

Glu Glu Thr Asp Ser Glu Pro Gln Ala Pro Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Isotope labeled CLN3 peptide 3
<220> FEATURE:
<221> NAME/KEY: MISC_FEATURE
<222> LOCATION: (10)..(10)
<223> OTHER INFORMATION: Isotope label

<400> SEQUENCE: 13

Glu Glu Thr Asp Ser Glu Pro Gln Ala Pro Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Isotope labeled CLN3 peptide 3
<220> FEATURE:
<221> NAME/KEY: MISC_FEATURE
<222> LOCATION: (10)..(10)
<223> OTHER INFORMATION: Isotope label
<220> FEATURE:
<221> NAME/KEY: MISC_FEATURE
<222> LOCATION: (11)..(11)
<223> OTHER INFORMATION: Isotope label

<400> SEQUENCE: 14

Glu Glu Thr Asp Ser Glu Pro Gln Ala Pro Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Isotope labeled CLN3 peptide 5
<220> FEATURE:
<221> NAME/KEY: MISC_FEATURE
<222> LOCATION: (14)..(14)
<223> OTHER INFORMATION: Isotope label

<400> SEQUENCE: 15

Phe Ser Asp Ser Glu Gly Glu Glu Thr Val Pro Glu Pro Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Isotope labeled CLN3 peptide 5
<220> FEATURE:
```

<221> NAME/KEY: MISC_FEATURE
<222> LOCATION: (13)..(13)
<223> OTHER INFORMATION: Isotope label

<400> SEQUENCE: 16

Phe Ser Asp Ser Glu Gly Glu Glu Thr Val Pro Glu Pro Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Isotope labeled CLN3 peptide 5
<220> FEATURE:
<221> NAME/KEY: MISC_FEATURE
<222> LOCATION: (13)..(13)
<223> OTHER INFORMATION: Isotope label
<220> FEATURE:
<221> NAME/KEY: MISC_FEATURE
<222> LOCATION: (14)..(14)
<223> OTHER INFORMATION: Isotope label

<400> SEQUENCE: 17

Phe Ser Asp Ser Glu Gly Glu Glu Thr Val Pro Glu Pro Arg
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Isotope labeled CLN3 peptide 7
<220> FEATURE:
<221> NAME/KEY: MISC_FEATURE
<222> LOCATION: (17)..(17)
<223> OTHER INFORMATION: Isotope label

<400> SEQUENCE: 18

Thr Glu Ala Pro Glu Ser Lys Pro Gly Ser Ser Ser Leu Ser Leu
1               5                   10                  15
Arg

<210> SEQ ID NO 19
<211> LENGTH: 17
<212> TYPE: PRT
<213> ORGANISM: Artificial Sequence
<220> FEATURE:
<223> OTHER INFORMATION: Isotope labeled CLN3 peptide 7
<220> FEATURE:
<221> NAME/KEY: MISC_FEATURE
<222> LOCATION: (16)..(16)
<223> OTHER INFORMATION: Isotope label

<400> SEQUENCE: 19

Thr Glu Ala Pro Glu Ser Lys Pro Gly Ser Ser Ser Leu Ser Leu
1               5                   10                  15
Arg

<210> SEQ ID NO 20
<211> LENGTH: 17
<212> TYPE: PRT
<213> ORGANISM: Artificial Sequence
<220> FEATURE:
<223> OTHER INFORMATION: Isotope labeled CLN3 peptide 7
<220> FEATURE:
<221> NAME/KEY: MISC_FEATURE
<222> LOCATION: (16)..(16)
<223> OTHER INFORMATION: Isotope label

```
<220> FEATURE:
<221> NAME/KEY: MISC_FEATURE
<222> LOCATION: (17)..(17)
<223> OTHER INFORMATION: Isotope label

<400> SEQUENCE: 20

Thr Glu Ala Pro Glu Ser Lys Pro Gly Ser Ser Ser Ser Leu Ser Leu
1               5                   10                  15

Arg
```